United States Patent
Howard et al.

(10) Patent No.: US 10,722,458 B2
(45) Date of Patent: *Jul. 28, 2020

(54) AMPHIPATHIC LIPID-BASED SUSTAINED RELEASE COMPOSITIONS

(71) Applicant: Pegasus Laboratories, Inc., Kansas City, MO (US)

(72) Inventors: Scott A. Howard, Pace, FL (US); Troy Purvis, Brandon, MS (US)

(73) Assignee: Pegasus Laboratories, Inc., Kansas City, MO (US)

( * ) Notice: Subject to any disclaimer, the term of this patent is extended or adjusted under 35 U.S.C. 154(b) by 3 days.

This patent is subject to a terminal disclaimer.

(21) Appl. No.: 13/907,180

(22) Filed: May 31, 2013

(65) Prior Publication Data
US 2013/0259937 A1 Oct. 3, 2013

Related U.S. Application Data

(63) Continuation-in-part of application No. 13/690,974, filed on Nov. 30, 2012, now Pat. No. 9,248,096.

(60) Provisional application No. 61/566,279, filed on Dec. 2, 2011.

(51) Int. Cl.
*A61K 9/00* (2006.01)
*A61K 9/20* (2006.01)

(52) U.S. Cl.
CPC .......... *A61K 9/0056* (2013.01); *A61K 9/2013* (2013.01)

(58) Field of Classification Search
CPC .............................. A61K 9/0056; A61K 9/2013
See application file for complete search history.

(56) References Cited

U.S. PATENT DOCUMENTS

| 4,241,091 | A | * | 12/1980 | Stroz | A23G 4/06 426/4 |
| 5,993,850 | A | | 11/1999 | Sankaram et al. | |
| 6,197,314 | B1 | | 3/2001 | Einig | |
| 6,730,322 | B1 | * | 5/2004 | Bernstein | A61K 9/1617 424/422 |
| 2005/0008701 | A1 | | 1/2005 | Sriwongjanva et al. | |
| 2005/0202072 | A1 | * | 9/2005 | Buch-Rasmussen | A61K 9/145 424/448 |
| 2006/0134208 | A1 | * | 6/2006 | Villa et al. | 424/468 |

(Continued)

FOREIGN PATENT DOCUMENTS

| WO | WO-1984-004674 | * 12/1984 |
| WO | 0033817 | 6/2000 |
| WO | WO-2006-010605 | * 2/2006 |

OTHER PUBLICATIONS

Sigma Aldrich, Thermal Transitions of homopolymers, Dec. 31, 1999.*

(Continued)

*Primary Examiner* — Aradhana Sasan
*Assistant Examiner* — Quanglong N Truong
(74) *Attorney, Agent, or Firm* — Hovey Williams LLP

(57) ABSTRACT

Chewable sustained release compositions and their methods of production are provided. The sustained release compositions contain amphipathic lipids and matrix-forming polymers, which are used to encapsulate various drugs and active ingredients. The chewable sustained release compositions can maintain their sustained release properties even after being fragmented into a plurality of pieces.

19 Claims, 5 Drawing Sheets

(56) References Cited

U.S. PATENT DOCUMENTS

| | | |
|---|---|---|
| 2007/0141096 A1 | 6/2007 | Van Lengerich |
| 2007/0298101 A1* | 12/2007 | Wiackowski et al. ........ 424/465 |
| 2008/0044454 A1* | 2/2008 | Yang ................... A61K 9/0056 424/439 |
| 2008/0220079 A1 | 9/2008 | Chen et al. |
| 2009/0081297 A1* | 3/2009 | Cook et al. .................. 424/489 |
| 2010/0062988 A1* | 3/2010 | Chen et al. ..................... 514/23 |
| 2010/0166810 A1 | 7/2010 | Habboushe |
| 2010/0178326 A1* | 7/2010 | Pinkhassik et al. .......... 424/450 |
| 2011/0288181 A1* | 11/2011 | Koltzenburg et al. ..... 514/772.1 |

OTHER PUBLICATIONS

Sigma Aldrich, polymer solutions, Dec. 31, 1999.*
The International Search Report and Written Opinion dated Mar. 27, 2013, in corresponding PCT/US2012/067361 filed on Nov. 30, 2012.
The Supplementary European Search Report dated Feb. 19, 2015, in EP 12854388 filed on Jun. 5, 2014.
The First Examination Report dated Mar. 16, 2015, in New Zealand Application 624641 filed May 7, 2014.
The Further Examination Report dated Oct. 21, 2015, in New Zealand Application 624641 filed May 7, 2014.
The Office Action dated Jul. 10, 20185, in EP Application No. 12 854 388.1.
Office Action in corresponding Brazil Patent Application No. BR112014013175-9, dated Jul. 3, 2019.

* cited by examiner

AMPHIPATHIC LIPID-BASED SUSTAINED RELEASE COMPOSITIONS

RELATED APPLICATIONS

The present application is a continuation-in-part of U.S. patent application Ser. No. 13/690,974 filed Nov. 30, 2012, which claims the benefit of U.S. Provisional Patent Application No. 61/566,279, filed Dec. 2, 2011, the entire disclosures of which are incorporated herein by reference.

BACKGROUND OF THE INVENTION

Field of the Invention

The present invention is directed to chewable sustained release compositions and to methods of preparing and using such compositions.

Description of the Related Art

Sustained release compositions have been developed to provide a slow and sustained release of a drug or active ingredient into a subject over an extended period of time. Thus, sustained release compositions mitigate the necessity for multiple daily dosings of certain drugs and other active ingredients. However, most existing sustained release compositions are not suitable as chewable formulations. In fact, chewing most sustained release compositions will inhibit their ability to slowly release the drug or active ingredient over an extended period of time and will result in an uncontrolled burst of the drug or active ingredient. Furthermore, most sustained release compositions have an unacceptable taste when chewed, which decreases the willingness of many patients to accept such tablets.

Chewable tablets of sustained release compositions have been increasingly utilized in various pharmaceutical and veterinary markets due to their ability to sustain constant drug release over an extended time period and maintain taste-masking properties even after being chewed into smaller fragments. For instance, chewable sustained release tablets have developed a niche in veterinary medicine because many of the treated animals tend to chew any medicine given orally. Chewable sustained release tablets are also increasingly being used in human medicine for patients who have difficulties in swallowing or taking intact medications.

Recently, wax-based agents have been incorporated into chewable sustained release compositions in an attempt to provide the desired sustained release and taste-masking properties. For instance, U.S. Patent Application Publication No. 2010/0062988 discloses chewable sustained release compositions produced by using dispersions of the vegetable protein zein coupled with wax-like agents and a spheronizing agent to encapsulate drugs and other active ingredients. The zein/wax matrix is able to produce a chewable sustained release composition that can add a degree of taste-masking to bitter tasting drugs. Similarly, U.S. Patent Application Publication No. 2008/0220079 utilizes wax-like agents in conjunction with a spherizonizing agent to produce a chewable sustained release composition that can encapsulate drugs and other active ingredients. However, the chewable sustained release compositions in both of these publications require that the compositions be heated to a temperature exceeding the melting points of the wax-like agent in order to effectively encapsulate the drug or active ingredient. Unfortunately, this additional heating step can increase the costs of producing these chewable sustained release compositions and potentially damage the encapsulated drug or active ingredient.

U.S. Patent Application Publication No. 2006/0134208 discloses various ingredients used in taste-masking formulations for controlled drug delivery. The low melting point fatty ingredients and amphiphilic ingredients described therein are kneaded or melted together with small amounts of solvent, then granulated into particulates. Following this granulation, the particles are then mixed together and suspended in a hydrophilic water-swellable matrix. The resulting formulations contain a lipophilic matrix surrounded by a hydrophilic matrix. Thus, two independent processes provide for the controlled release mechanism in U.S. 2006/0134208: (1) the dissolution of the hydrophilic matrix and (2) the erosion of the lipophilic matrix. However, the amphiphilic ingredients listed in U.S. 2006/0134208 are not dissolved or dispersed in an alcoholic or hydroalcoholic solution when producing the formulations. Therefore, the amphiphilic ingredients described therein are not contained in a single continuum and do not function as a solid state plasticizer for the ingredients in the lipophilic matrix. Consequently, the separate lipophilic and hydrophilic matrices produced using this process cannot maintain sustained release characteristics when broken or chewed.

Accordingly, there is a need for a chewable sustained release composition, and a process for making such, that is capable of maintaining a sustained release of a drug or active ingredient over an extended time period and that exhibits certain taste-masking properties.

SUMMARY OF INVENTION

In one embodiment of the present invention, a sustained release composition is provided. The sustained release composition comprises (a) one or more active ingredients; (b) one or more amphipathic lipids; and (c) at least one bulking or spheronizing agent. The active ingredients are encapsulated within a matrix comprising the amphipathic lipids and the bulking or spheronizing agent. The composition exhibits an in vitro dissolution rate of the active ingredients, as measured by a USP Dissolution Apparatus II, of about 10% to 50% after about 2 hours, about 25% to 90% after about 4 hours, more than about 60% after about 12 hours, and more than about 75% after about 16 hours. Additionally, the average in vitro dissolution rate of the composition as measured by a USP Dissolution Apparatus II does not increase by more than 100% during the first 2 hours after the composition has been fragmented into two or more pieces.

In another embodiment of the present invention, a sustained release composition is provided. The sustained release composition comprises (a) one or more active ingredients; (b) one or more amphipathic lipids; (c) at least one bulking or spheronizing agent, and (d) at least one plasticized matrix-forming polymer. The active ingredients are encapsulated within a matrix comprising the amphipathic lipids and the matrix-forming polymer. The composition exhibits an in vitro dissolution rate of the active ingredients, as measured by a USP Dissolution Apparatus II, of about 10% to 90% after about 2 hours, about 20% to 90% after about 4 hours, more than about 60% after about 12 hours, and more than about 70% after about 16 hours.

In yet another embodiment of the present invention, a process to produce a sustained release composition is provided. The process comprises the steps of: (a) combining one or more active ingredients, one or more amphipathic lipids, and at least one matrix-forming polymer in a solvent to produce an active-containing solution or suspension; (b) mixing the active-containing solution or suspension with at least one spheronizing or bulking agent to produce a mixture; and (c) forming the mixture into tablets. The tablets exhibit an in vitro dissolution rate of the active ingredients, as measured by a USP Dissolution Apparatus II, of about 10% to 90% after about 2 hours, about 20% to 90% after about 4 hours, more than about 60% after about 12 hours, and more than about 70% after about 16 hours. In addition, steps (a)-(c) are performed at temperatures that do not exceed the melting points of the lipids. Furthermore, step (a) is performed at a temperature exceeding the glass transition temperature of the matrix-forming polymer.

DETAILED DESCRIPTION

Figure 1:
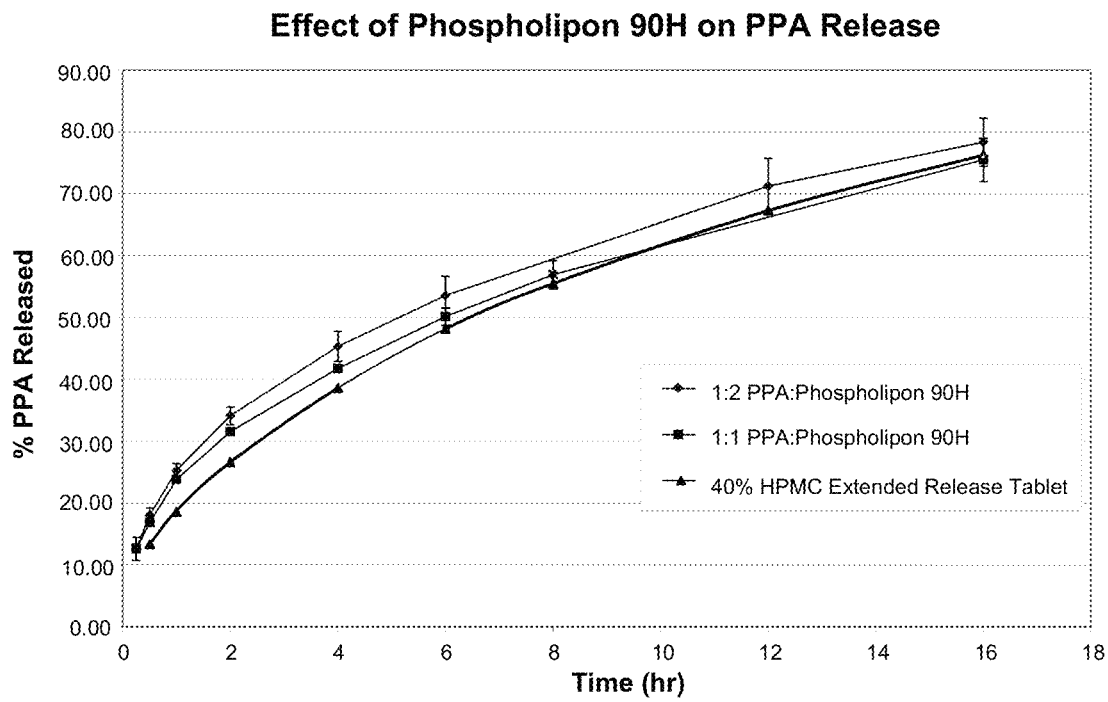
FIG. 1 depicts in vitro dissolution profiles of phenylpropanolamine HCl ("PPA") sustained release tablets at two different phospholipid concentrations as compared to PPA extended release tablets containing hypromellose.

The present disclosure is directed to chewable sustained release compositions that comprise at least one amphipathic lipid. An "amphipathic lipid," as used herein, pertains to any molecule that is lipophilic and has at least one region that is polar or ionic (i.e., hydrophilic). The sustained release compositions of the present disclosure can comprise, consist essentially of, or consist of: (i) at least one active ingredient, (ii) at least one amphipathic lipid, and (iii) at least one bulking and/or spheronizing agent. Furthermore, the sustained released composition of the present disclosure can take the form of tablets or multiparticulates. In certain embodiments, the sustained release compositions provided herein are capable of maintaining the sustained release of active ingredients subsequent to chewing or being fragmented into smaller pieces. In other embodiments, the compositions of the present disclosure have minimal initial burst of active ingredients to enable the making of taste-masking formulations.

Unless indicated otherwise, any weight percentage is the weight of the listed component relative to the total weight of a composition, to the total weight of a tablet, or to the total weight of a multiparticulate.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used in the present disclosure, the term "about" refers to any value in the range of 90% to 110% of the specified value.

Amphipathic Lipids

The sustained release composition of the present disclosure comprises one or more amphipathic lipids. In certain embodiments, the amphipathic lipids can comprise at least about 0.5, 1, 2, 3, 4, 5, 6, 7, 8, 9, 10, 15, 20, 25, 30, 35, 40, 45, or 50 weight percent of the composition, tablet, or multiparticulate. Additionally or alternatively, the amphipathic lipids can comprise no more than about 80, 75, 70, 65, 60, 55, 50, 45, 40, 35, 30, 25, 20, 15, 10, or 5 weight percent of the composition, tablet, or multiparticulate.

In one embodiment, the amphipathic lipids can include any lipid that exhibits both hydrophilic and lipophilic properties. In certain embodiments, the amphipathic lipids are selected from the group consisting of phospholipids, lecithins, steroids, sphingolipids, ceramides, and glycolipids. In a more particular embodiment, the amphipathic lipids are selected from the group consisting of phospholipids and lecithins. In one embodiment, the amphipathic lipids do not include lipids formed from hydrophobic polymers and/or hydrophilic polymers.

Phospholipids are amphipathic lipids that generally contain lipophilic hydrocarbon tails and a hydrophilic head comprising a phosphate group. Due to this hydrophilic head, phospholipids can be readily soluble or dispersable in various organic solvents. Lecithin is generally an unrefined mixture of phospholipids that contains a non-defined ratio of phosphatidylcholine. The ratio of phosphatidylcholine in the lecithin depends on the source of the lecithin.

In one embodiment, the phospholipids comprise phosphatidylcholine, phosphatidylethanol, phosphatidylserine, or mixtures thereof. In another embodiment, the phospholipids comprise at least about 5, 10, 15, or 20 and/or not more than 99, 95, or 90 weight percent of phosphatidylcholine. Exemplary phospholipids include, for example, PHOSPHOLIPON 90H and PHOSPHOLIPON 20 from LIPOID (Newark, N.J.). Exemplary lecithins include, for example, ULTRALEC from ARCHER DANIELS MIDLAND (Decatur, Ill.) and lecithin from BULKFOODS.COM (Toledo, Ohio).

Steroids are amphipathic lipids that generally contain a base structure of at least four cycloalkane rings that are joined together. Various functional groups can be attached to this four ring core in order to impart hydrophilic properties onto the steroid. Exemplary steroids include, for example, cholesterol.

The amphipathic lipids can include, for example, lipids that are suspended, dispersed, or dissolved in an aqueous, hydroalcoholic, or organic solvent. In one embodiment, the amphipathic lipids can be suspended, dispersed, or dissolved in a solvent selected from the group consisting of water, methanol, ethanol, n-propanol, isopropanol, t-butanol, ethyl acetate, acetone, and mixtures thereof. In an alternative embodiment, the amphipathic lipids do not include solutions of polymers in organic solvents.

In certain embodiments, the amphipathic lipids are not exposed to any temperatures that exceed their melting points during the production of the sustained release compositions. For example, during production of the sustained release compositions, the amphipathic lipids may not be subjected to temperatures exceeding 120° C., 110° C., 100° C., 90° C., 80° C., 70° C., 60° C., 50° C., 40° C., 35° C., or 30° C. Unlike conventional wax-based lipids, amphipathic lipids do not need to be melted in any degree in order to effectively encapsulate the active ingredients. The absence of a heating step can reduce production costs and minimize potential degradation to the active ingredients during production.

It is theorized that the mechanism involved in this disclosure is based on the formation of a solid matrix comprising amphipathic lipids and one or more matrix-forming polymers that encapsulate an active ingredient. The amphipathic lipids "seal" the active ingredients by embedding the active ingredient in the encapsulating matrix. Furthermore, the amphipathic lipids can plasticize the matrix-forming polymers to thereby lower the glass transition temperature of these components. For clarification, the amphipathic lipids of this disclosure are not used as a coating.

In certain embodiments, the amphipathic lipids can function as a solid state plasticizer in the sustained release compositions. One advantage of a solid state plasticizer is that it can be harder to leach out of a resulting material. In contrast, the leaching of liquid plasticizers from formed films can affect the stability of the film over time and consequently affect the controlled release of the active ingredients. Furthermore, common liquid plasticizers, such as phthalates, are hazardous estrogen mimicers (Heudorf et al., "Phthalates: toxicology and exposure" *Int J Hyg Environ Health* 210 (5): 623-34). On the contrary, the amphipathic lipids, such as phospholipids, are safe, naturally-occurring, biologically-compatible compounds that have been shown to plasticize and reduce the glass transition temperature of certain film barriers (Frohoff-Hülsmann et al. *Eur J Pharm Biopharm.* 1999 July; 48(1):67-75).

Active Ingredients

As used in the present disclosure, the term "active ingredient" includes any active pharmaceutical ingredient(s) and nutraceutical ingredient(s). The active ingredients in the composition may be any active ingredients (i.e., a compound or a composition) with beneficial pharmaceutical, therapeutic, nutritional, or cosmetic effects. The active ingredients can comprise at least about 0.5, 1, 2, 3, 4, 5, 6, 7, 8, 9, 10, 15, 20, 25, 30, 35, 40, 45, 50, 55, or 60 weight percent of the composition, tablet, or multiparticulate. Additionally or alternatively, the active ingredients can comprise no more than about 95, 90, 85, 80, 75, 70, 65, 60, 55, 50, 45, 40, 35, 30, 25, 20, 15, or 10 weight percent of the composition, tablet, or multiparticulate.

In certain embodiments, the active ingredient is phenylpropanolamine ("PPA") or its pharmaceutically acceptable salt (e.g., phenylpropanolamine hydrochloride). PPA has been used as a decongestant and an appetite suppressant in humans. In veterinary medicine, it is also used to control urinary incontinence in dogs.

In certain embodiments, the active ingredient may be one or more analgesics or pharmaceutically acceptable salts thereof, such as acetaminophen, a centrally acting analgesic agent, opiate, narcotic, nonsteroidal anti-inflammatory drugs ("NSAID"), and/or salicylate. Exemplary NSAIDs include, for example, aspirin, carprofen, deracoxib, etodolac, firocoxib, celecoxib, diclofenac, diflunisal, flurbiprofen, ibuprofen, indomethacin, ketoprofen, kietorolac, mefenamic acid, meloxicam, naproxen, phenylbutazone, piroxicam, rofecoxib, sulindac, tepoxalin, valdecoxib, and/or vedaprofen.

In certain embodiments, the active ingredient may be one or more medications for treating respiratory congestion, allergy symptoms, nasal discharge, or tussis. These include, for example, bromopheniramine, chlorpheniramine, dextromethorphan, diphenhydramine, ephedrine, guaifenesin, PPA, pseudoephedrine, and/or acceptable salts thereof.

In certain embodiments, the active ingredient may be an anti-epileptic, anti-seizure, anti-convulsant, or GABA-ergics. These include, for example, barbiturates, benzodiazepines, carbamates, carbamazepines, gabapentin, oxazolidinediones, phenyloin, potassium bromide, pregabalin, pyrrolidines, succinimides, sulfonamides, triazines, topiramate, valproamines, zonisamide, and/or acceptable salts thereof.

In certain embodiments, the active ingredient is a dietary supplement or nutraceutical, such as vitamins, multi-vitamins (i.e., a mixture of multiple vitamins, such as a mixture of two or more fat-soluble vitamins, a mixture of two or more water-soluble vitamins, and a mixture of one or more fat-soluble vitamins and one or more water-soluble vitamins), minerals, herbs or other botanicals, amino acids, proteins (e.g., milk protein concentrates), antioxidants (e.g., grape seed extract and milk thistle), anti-inflammatory agents (e.g., bromelain), carotenoids (e.g., lycopene and lutein), flavonoids (e.g., quercetin and rutin), prebiotics (e.g., arabinogalactan and fructooligosaccharides), and/or weight loss agents (e.g., *garcinia cambogia*).

In certain embodiments, the active ingredient is one or more anti-infective or anti-microbial agents or pharmaceutically acceptable salts thereof including, for example, β-lactam antibiotics (e.g., amoxicillin, ampicillin, and ceftiofur), lincosamides, clindamycin, aminoglycosides, cephalosporins, macrolides, ketolides, penicillins, quinolones, sulfonamides, tetracyclines (e.g., doxycycline), cycloserine, vancomycin, linezolid, oxazolidinone, pyrimethamine, atovaquone, tigecycline, glycylcyclines, anthelmintics, antifungals, antimalarial agents, antiprotozoal agents, leprostatics, antituberculosis agents, and/or antiparasitics. In other embodiments, the anti-infective agent is azithromycin, clarithromycin, roxithromycin, erythromycin, telithromycin, ciprofloxacin, a combination of amoxicillin and clavulanate potassium, and/or a pharmaceutically acceptable salt thereof.

In certain embodiments, the active ingredient is a thyroid or a thyroid modulating agent, including levothyroxine sodium useful for treating hypothyroidism and methimazole useful for treating hyperthyroidism.

In certain embodiments, the active ingredient is a behavior modifying drug, such as anti-anxiety agents and antidepressants. Exemplary behavior modifying drugs include, for example, buspirone hydrochloride, fluoxetine hydrochloride, paroxetine, amitriptyline hydrochloride, clomipramine hydrochloride, doxepin, and imipramine hydrochloride.

In certain embodiments, the active ingredient is an anti-diabetic agent. Exemplary anti-diabetic agents include, for example, glipizide, metformin, acarbose, and glibenclamide.

In certain embodiments, the active ingredient is a phosphate binding compound. Exemplary compounds include, for example, sevelamer hydrochloride, aluminum carbonate, and aluminum hydroxide.

In certain embodiments, the active ingredient is one or more antiviral agents or a pharmaceutically acceptable salt thereof, such as, for example, abacavir, acyclovir, ganciclovir, lammivudine, nelfinavir, ritonavir, valacyclovir, and zidovudine.

In certain embodiments, the active ingredient is an antacid such as, for example, sodium antacids (e.g., trisodium phosphate), calcium antacids (e.g., calcium carbonate), aluminum antacids (e.g., aluminum hydroxide), magnesium antacids (e.g., magnesium hydroxide), and combinations thereof.

In certain embodiments, the active ingredient is one or more insect growth regulators ("IGR") or pharmaceutically acceptable salts thereof such as, for example, methoprene, kinoprene, hydroprene, diflubenzuron, and/or pyriproxifen.

In certain embodiments, the active ingredient is one or more antioxidants or pharmaceutically acceptable salts thereof such as, for example, ascorbic acid, bromelain, grapeseed extract, milk thistle, rose hip, alpha lipoic acid, beta carotene, lycopene, lutein, and/or alpha tocopherol.

In certain embodiments, the active ingredient is a high dose active ingredient. An active ingredient of "high dose" refers to an active ingredient that is orally administered at a daily dose of about or greater than 1 mg/kg body weight to an adult human patient or an adult non-human subject. In one embodiment, the active ingredient has a daily dose about or greater than 2, 3, 4, 5, 6, 7, 8, 9, 10, 20, 30, 40, or 50 mg/kg body weight for an adult human or an adult non-human subject. In another embodiment, the active ingredient has a daily dose about or greater than 100, 200, 250, 300, 350, 400, 450, 500, 600, 700, 800, 900, or 1000 mg for an adult human or an adult non-human subject. In yet another embodiment, the active ingredients are those that must be given at about 200 mg, 300 mg, 400 mg, 500 mg, 600 mg, 700 mg, 800 mg, 900 mg, or 1 g per dose in a twice-a-day, once-a-day, or once-per-treatment regimen.

Exemplary active ingredients of high dose include, for example, guaifenesin (100 mg/dose or more), acyclovir (200 mg/dose), acetaminophen (300 mg/dose), metformin (500 mg/dose), gabapentin (100-800 mg/dose), glucosamine, glucosamine sulfate, and glucosamine HCl (500 mg/dose).

In certain embodiments, the active ingredient has a short half-life. An active ingredient of "short half-life" refers to an active ingredient that has a half-life about or less than 12 hours. In other embodiments, the active ingredient of the present disclosure has a half-life of about or less than about 11, 10, 9, 8, 7, 6, 5, 4, 3, or 2 hours in a human or non-human subject. In general, an active ingredient of a short half-life is required to be taken more than twice a day in its immediate release forms to maintain the efficacious blood concentration level through the day.

In certain embodiments, the active ingredient may be insoluble, slightly soluble, sparingly soluble, soluble, freely soluble, or very soluble in water.

In certain embodiments, the composition may further comprise a second active ingredient. In one embodiment, the other active ingredient may have the same or similar pharmacological effect as the first active ingredient. In another embodiment, the second active ingredient may have a pharmacological effect different from the first active ingredient.

Secondary Sustained Release Agent

In certain embodiments, a secondary sustained release agent can be added to the composition in order to supplement and reinforce the amphipathic lipids. In such an embodiment, the secondary sustained release agent comprises at least about 0.5, 1, 2, 3, 4, 5, 6, 7, 8, 9, 10, 15, 20, 25, 30, 35, 40, 45, or 50 weight percent of the composition, tablet, or multiparticulate. Additionally or alternatively, the secondary sustained release agent can comprise no more than about 80, 75, 70, 65, 60, 55, 50, 45, 40, 35, 30, 25, 20, 15, 10, or 5 weight percent of the composition, tablet, or multiparticulate.

In one embodiment, the secondary sustained release agent is different from the amphipathic lipids. The secondary sustained release agent can comprise, for example, esters of a fatty alcohol and a saturated and/or unsaturated fatty acid, saturated and unsaturated fatty acid glycerides (mono-, di-, or triglycerides), hydrogenated fats, hydrogenated vegetable oils, cholesterol, hydrocarbons, waxes, hydrophobic polymers having a hydrocarbon backbone, hydrophilic polymers having a hydrocarbon backbone, or a combination thereof.

In one embodiment, the secondary sustained release agent comprises a wax, such as animal and insect waxes (e.g., beeswax, Chinese wax, shellac wax, spermaceti wax, and lanolin wax), vegetable waxes (e.g., bayberry wax, candelilla wax, carnauba wax, castor wax, esparto wax, Japan wax, jojoba oil, ouricury wax, and rice bran wax), mineral waxes (e.g., ceresin waxes, montan wax extracted from lignite and brown coal, ozocerite, and peat waxes), petroleum waxes (e.g., paraffin wax and microcrystalline wax), and/or synthetic waxes (e.g., polyethylene waxes, chemically modified waxes, substituted amide waxes, and polymerized alpha-olefins).

In another embodiment, the secondary sustained release agent comprises vegetable wax, candelilla wax, carnauba wax, castor wax, esparto wax, Japan wax, jojoba oil, ouricury wax, and/or rice bran wax.

In yet another embodiment, the secondary sustained release agent comprises hydrogenated vegetable oils such as, for example, hydrogenated cottonseed oil, partially hydrogenated cottonseed oil, hydrogenated soybean oil, partially hydrogenated soybean oil, and stearyl alcohol.

Bulking or Spheronizing Agents

The sustained release compositions of the present disclosure also comprise one or more bulking or spheronizing agents. The bulking or spheronizing agents can comprise at least about 0.1, 0.5, 1, 3, 5, 10, 15, 20, 25, 30, 40, 45, or 50 weight percent of the composition, tablet, or multiparticulate. Additionally or alternatively, the bulking or spheronizing agent can comprise no more than about 95, 90, 85, 80, 75, 70, 65, 60, 55, 50, 40, 30, 20, or 10 weight percent of the composition, tablet, or multiparticulate.

A "bulking agent," as used herein, refers to an agent that enhances the ability of the sustained release composition to form into a cohesive plastic mass that can subsequently be granulated or extruded and compressed into tablets.

A "spheronizing agent," as used herein, refers to an agent that enhances the ability of the sustained release composition to form into a cohesive plastic mass that may be subsequently spheronized to produce spherical pellets or fragmented to form non-spherical pellets.

In one embodiment, the bulking or spheronizing agent is selected from a group consisting of microcrystalline cellulose, starch, sodium carboxymethylcellulose, pregelatinized starch, dicalcium phosphate, powdered sugar, calcium phosphate, calcium sulfate, lactose, mannitol, kaolin, sodium chloride, sorbitol, and combinations thereof. In certain embodiments, the bulking or spheronizing agent is microcrystalline cellulose. In other embodiments, the bulking or spheronizing agent is a combination of microcrystalline cellulose and dicalcium phosphate. In various embodiments, the bulking or spheronizing agent comprises a polymeric structure. In certain embodiments, the bulking or spheronizing agent is a "matrix-forming" polymer that can form a matrix within the sustained release composition.

In certain embodiments, the amphipathic lipids can function as a plasticizer for the bulking or spheronizing agents. In such embodiments, the amphipathic lipids can reduce the glass transition temperature ("Tg") of the bulking or spheronizing agents by at least about 5%, 10%, 15%, 20%, 25%, 30%, 35%, 40%, 45%, 50%, or 55% compared to the non-plasticized Tg of the bulking or spheronizing agents. In one or more embodiments, the amphipathic lipids can lower the Tg of the bulking or spheronizing agents by at least about 10° C., 15° C., 20° C., 25° C., 30° C., 35° C., 40° C., 45° C., 50° C., 55° C., 60° C., 65° C., 70° C., 75° C., 80° C., 85° C., 90° C., or 95° C. In various embodiments, when the amphipathic lipids function as a plasticizer for the bulking or spheronizing agents, the plasticized bulking or spheronizing agents can have a Tg of at least about 25° C., 30° C., 35° C., 40° C., 45° C., 50° C., 55° C., 60° C., or 65° C. and/or not more than 150° C., 140° C., 130° C., 120° C., 110° C., 100° C., 90° C., 80° C., or 70° C. as measured using Differential Scanning calorimetry ("DSC"). Thus, in one or more embodiments, the sustained release composition comprises at least one or more plasticized bulking or spheronizing agents.

Sustained Release

The sustained release composition of the present disclosure provides sustained release of the active ingredient. The term "sustained release," as used herein, refers to a release of an active ingredient that occurs more slowly relative to an immediate release dosage form. The term may be used interchangeably with "slow-release," "controlled release," "modified release," or "extended release." The sustained release property of a composition is typically measured by an in vitro dissolution method and confirmed by an in vivo blood concentration-time profile (i.e., a pharmacokinetic profile).

The term "immediate release dosage forms" refers to release forms wherein at least 75% of the active ingredient is released or dissolved within about one-half hour after in vivo administration or in an in vitro dissolution assay as known in the art or tested using a USP Dissolution Apparatus II.

In certain embodiments, the sustained release composition releases the active ingredient in a nearly linear fashion for at least about 2, 3, 4, 5, 6, 7, 8, 9, 10, 11, 12, 14, or 16 hours. An active ingredient is released in a "nearly linear" fashion for a specified period of time if the release rate of the agent does not change more than 20% during each hour within the specified period of time.

In certain embodiments, the sustained release composition has an in vitro dissolution rate, as measured by a USP Dissolution Apparatus II, of at least about 5%, 10%, 15%, 20%, 25%, or 30% of the active ingredient released after 2 hours, at least about 10%, 15%, 20%, 25%, 30%, 35%, or 40% of the active ingredient released after 4 hours, at least about 20%, 25%, 30%, 35%, 40%, 45%, or 50% of the active ingredient released after 6 hours, at least about 25%, 30%, 35%, 40%, 45%, or 50% of the active ingredient released after 8 hours, at least about 30%, 35%, 40%, 45%, 50%, or 55% of the active ingredient released after 10 hours, at least about 35%, 40%, 45%, 50%, 55%, 60%, 65%, or 70% of the active ingredient released after 12 hours, and/or at least about 40%, 45%, 50%, 55%, 60%, 65%, 70%, 75%, or 80% of the active ingredient released after 16 hours.

In certain embodiments, the sustained release composition has an in vitro dissolution rate, as measured by a USP Dissolution Apparatus II, of no more than about 10%, 20%, 30%, 40%, 50%, 60%, 70%, 80%, or 90% of the active ingredient released after 2 hours, no more than about 20%, 30%, 40%, 50%, 60%, 70%, 80%, or 90% of the active ingredient released after 4 hours, no more than about 30%, 40%, 50%, 60%, 70%, 80%, or 90% of the active ingredient released after 6 hours, no more than about 40%, 50%, 60%, 70%, 80%, or 90% of the active ingredient released after 8 hours, no more than about 50%, 60%, 70%, 80%, or 90% of the active ingredient released after 10 hours, no more than about 60%, 70%, 80%, or 90% of the active ingredient released after 12 hours, and/or no more than about 70%, 80%, or 90% of the active ingredient released after 16 hours.

The term "initial burst" refers to uncontrolled or quick release of the active ingredient (e.g., greater than 10% of the drug load) from a dosage form immediately following an exposure to an aqueous medium (such as saliva or gastric fluid). A burst is undesired as it defeats the purpose of a sustained release and/or taste-masking for a chewable composition.

In certain embodiments, the sustained release composition can have minimal initial burst of no more than about 10%, 9%, 8%, 7%, 6%, 5%, 4%, 3%, 2% or 1% during the first 1 to 5 minutes as measured in an in vitro dissolution assay by a USP Dissolution Apparatus II. Such a feature allows the making of taste-masking formulations, especially desirable for active ingredients with unpleasant tastes (e.g., phenylpropanolamine, ibuprofen, acetaminophen, and certain vitamins).

In certain embodiments, the sustained release compositions do not exhibit a "delayed" dissolution profile. As used herein, "delayed dissolution profile" refers to situations when the sustained release composition has been introduced into an environment and does not immediately begin to release the active ingredient therein due to a dissolution inhibiting factor of the environment into which the composition is introduced. These inhibiting factors of the environment can include, for example, the pH, temperature, or a combination thereof. In various embodiments, the sustained release composition does not exhibit a delayed dissolution profile and can begin releasing the active ingredient immediately upon entering an environment regardless of the environmental conditions. For example, upon being released in an environment, the sustained release composition can exhibit an in vitro dissolution rate, as measured by a USP Dissolution Apparatus II, of at least about 1%, 2%, 3%, 4%, 5%, 6%, 7%, 8%, 9%, or 10% of the active ingredient released after one hour. In one or more embodiments, the sustained release compositions can exhibit such non-delayed dissolution profiles in environments having a pH of less than about 7, 6, 5, 4, 3, or 2 and/or greater than about 7, 8, 9, 10, 11, 12, or 13.

In certain embodiments, the sustained release compositions are chewable. "Chewable," as used herein, refers to the ability of a tablet or multiparticulate composition to maintain its sustained release property and taste-masking property if fragmented into a plurality of smaller pieces.

In certain embodiments, when the tablets or multiparticulates are broken into a plurality of fragments, the fragmented composition can maintain an in vitro dissolution rate of the active ingredient, as measured by a USP Dissolution Apparatus II, of no more than about 90%, 80%, 70%, 60%, 50%, 40%, 30%, or 20% of the active ingredient released after 2, 3, 4, 5, 6, 7, 8, 9, 10, 11, or 12 hours. In various embodiments, the tablets or multiparticulates can be broken into two or more fragments. In such embodiments, each of the fragments can have the same or substantially the same dissolution profile as the original, non-fragmented tablets or multiparticulates. As used herein, the term "substantially the same" in reference to dissolution profiles means that the fragments possess a dissolution profile that departs from the dissolution profile of the unfragmented tablet or multiparticulate by no more than about 10%, 8%, 6%, 5%, 4%, 2%, or 1%.

In certain embodiments, the average in vitro dissolution rate of the non-fragmented sustained release composition in tablet or multiparticulate forms, as measured by a USP Dissolution Apparatus II, does not increase by more than about 100%, 90%, 80%, 70%, 60%, 50%, 40%, 30%, 20%, 10%, 5%, or 1% during the first 1, 2, 3, 4, 5, 6, 7, 8, 9, 10, 11, or 12 hours after the tablets or pellets have been fragmented into two or more fragments.

In certain embodiments, the sustained release composition, when administered orally to a patient in need of the equivalent daily dose of an immediate release formulation, provides a plasma concentration of its active ingredient at or above its minimum effective concentration for a period of time at least about the same as, or about 1.5, 2, 3, 4, or 5 times of, that of the immediate release formulation administered at a daily standard dose (i.e., the daily dose according to the official product description for the formulation or the dose approved by a regulatory authority for the formulation).

Multiparticulates

In certain embodiments, the sustained release composition is in the form of multiparticulates, which are discrete particles that make up a multiple-unit dosage form. Multiparticulates include, for example, pellets (e.g., spherical or non-spherical pellets) and granules.

The term "pellets" refers to small particles with approximately uniform shapes and sizes produced by an extrusion process. A "small particle" refers to a particle of which diameter, length, height, and width is at most 10 mm (e.g., at most 2, 3, 4, 5, 6, 7, 8, or 9 mm).

In certain embodiments, the composition of the present disclosure is in the form of spherical pellets. The term "spherical pellet" refers to beads, beadlets, spherical particles, spheroids, or the like that are of round or about round in shape and are generally made by an extrusion and spheronization process.

Additional Ingredients and Coatings

Optionally, the sustained release composition may comprise one or more excipients, including binders, antioxidants, colorants, lubricants, glidants, and flavoring agents. In one embodiment, the excipients can comprise at least about 0.1, 1, 5, 10, or 15 and/or no more than about 50, 40, 25, 20, 15, or 10 percent by weight of the composition, tablet, or multiparticulate.

Suitable binders include water-soluble hydroxyalkyl celluloses such as povidone, polyvinylpyrrolidone, xanthan gum, cellulose gums (e.g., hydroxypropyl cellulose, hydroxypropyl methylcellulose ("HPMC"), and sodium carboxymethylcellulose sodium ("CMC")), collagen, proteins, gelatin, starch, and/or water-insoluble polymers (e.g., pregelatinized starch, acrylic polymers or copolymers, or alkyl celluloses such as ethylcellulose). In various embodiments, the binder is a "matrix-forming" polymer that can form a matrix within the sustained release composition. In certain embodiments, the sustained release composition can comprise at least about 0.1, 0.5, 1, 2, 3, 4, or 5 and/or not more than about 50, 40, 30, 20, 10, or 6 weight percent of one or more binders. In one or more embodiments, the binder comprises a polymeric binder. In one embodiment, the binder comprises an alkyl cellulose. In another embodiment, the binder comprises ethylcellulose.

The binders used herein can exhibit a Tg of at least about 100° C., 110° C., 120° C., 130° C., 140° C., 150° C., or 160° C. and/or not more than 250° C., 240° C., 230° C., 220° C., 210° C., 200° C., 190° C., or 180° C. as measured using DSC. In certain embodiments, the amphipathic lipids can function as a plasticizer for the binders. In such embodiments, the amphipathic lipids can reduce the Tg of the binder by at least about 5%, 10%, 15%, 20%, 25%, 30%, 35%, 40%, 45%, 50%, or 55% compared to the non-plasticized Tg of the binder. In one or more embodiments, the amphipathic lipids can lower the Tg of the binder by at least about 10° C., 15° C., 20° C., 25° C., 30° C., 35° C., 40° C., 45° C., 50° C., 55° C., 60° C., 65° C., 70° C., 75° C., 80° C., 85° C., 90° C., or 95° C. In various embodiments, when the amphipathic lipids function as a plasticizer for the binder, the plasticized binder can have a Tg of at least about 25° C., 30° C., 35° C., 40° C., 45° C., 50° C., 55° C., 60° C., or 65° C. and/or not more than 150° C., 140° C., 130° C., 120° C., 110° C., 100° C., 90° C., 80° C., or 70° C. as measured using DSC. Thus, in one or more embodiments, the sustained release composition comprises at least one or more plasticized binders.

Suitable antioxidants include butylated hydroxyanisole ("BHA"), butylated hydroxytoluene ("BHT"), vitamin E, and/or ascorbyl palmitate.

Suitable colorants may be selected from any FD&C pigments or dyes.

Suitable lubricants include talc, stearic acid, vegetable oil, calcium stearate, zinc stearate, and/or magnesium stearate.

Suitable glidants include talc, silicon dioxide, and cornstarch.

Suitable flavoring agents include, for example, liver blend flavorings, roast beef flavorings, garlic flavorings, and any other flavoring known in the art. In various embodiments, the flavoring agents contain certain carbohydrates and/or proteins that are polymers. In such embodiments, the flavoring agents can comprise a "matrix-forming" polymer that can form a matrix within the sustained release composition. In certain embodiments, the sustained release composition can comprise at least about 0.1, 0.5, 1, 2, 3, 4, or 5 and/or not more than about 50, 40, 30, 20, 10, or 6 weight percent of one or more flavoring agents. In one or more embodiments, the flavoring agents comprise a liver blend containing collagen.

In certain embodiments, the amphipathic lipids can function as a plasticizer for the flavoring agents when such components contain a polymeric component. In such embodiments, the amphipathic lipids can reduce the Tg of the flavoring agents by at least about 5%, 10%, 15%, 20%, 25%, 30%, 35%, 40%, 45%, 50%, or 55% compared to the non-plasticized Tg of the flavoring agents. In one or more embodiments, the amphipathic lipids can lower the Tg of the flavoring agents by at least about 10° C., 15° C., 20° C., 25° C., 30° C., 35° C., 40° C., 45° C., 50° C., 55° C., 60° C., 65° C., 70° C., 75° C., 80° C., 85° C., 90° C., or 95° C. In various embodiments, when the amphipathic lipids function as a plasticizer for the flavoring agents, the plasticized flavoring agents can have a Tg of at least about 25° C., 30° C., 35° C., 40° C., 45° C., 50° C., 55° C., 60° C., or 65° C. and/or not more than 150° C., 140° C., 130° C., 120° C., 110° C., 100° C., 90° C., 80° C., or 70° C. as measured using DSC. Thus, in one or more embodiments, the sustained release composition comprises at least one or more plasticized flavoring agents.

Other excipients that may be incorporated into the sustained release compositions include preservatives or any other excipient commonly used in the pharmaceutical industry.

In certain embodiments, the composition of the present disclosure is optionally coated for additional drug release control, appearance, moisture protection, taste, or flavor improvement.

The term "sustained release barrier coating" refers to a coating on the tablets or multiparticulates that substantially slows the release of the active ingredient. More specifically, the presence of a sustained release barrier coating reduces the in vitro dissolution rate of the active ingredient within the first two hours by at least about 50%.

Suitable sustained release coating materials can include, for example, water-insoluble waxes and polymers such as hydrogenated vegetable oil (e.g., hydrogenated cottonseed oil), polymethacrylates, glyceryl behenate, and/or water-insoluble cellulosics (e.g., ethylcellulose). In various embodiments, the sustained release coating materials can be added during the production of the sustained release composition and thereby act as a "matrix-forming" polymer. In such embodiments, the sustained release coating materials can form a matrix within the sustained release composition. In certain embodiments, the sustained release composition can comprise at least about 0.1, 0.5, 1, 2, 3, 4, or 5 and/or not more than about 50, 40, 30, 20, 10, or 6 weight percent of one or more sustained release coating materials. In one embodiment, the sustained release composition comprises ethylcellulose.

The sustained release coating materials used herein can exhibit a Tg of at least 100° C., 110° C., 120° C., 130° C., 140° C., 150° C., or 160° C. and/or not more than 250° C., 240° C., 230° C., 220° C., 210° C., 200° C., 190° C., or 180° C. as measured using DSC. In certain embodiments, when the sustained release coating materials contain a polymeric component, the amphipathic lipids can function as a plasticizer for the sustained release coating materials. In such embodiments, the amphipathic lipids can reduce the Tg of the sustained release coating materials by at least 5%, 10%, 15%, 20%, 25%, 30%, 35%, 40%, 45%, 50%, or 55% compared to the non-plasticized Tg of the sustained release coating materials. In one or more embodiments, the amphipathic lipids can lower the Tg of the sustained release coating materials by at least 10° C., 15° C., 20° C., 25° C., 30° C., 35° C., 40° C., 45° C., 50° C., 55° C., 60° C., 65° C., 70° C., 75° C., 80° C., 85° C., 90° C., or 95° C. In various embodiments, when the amphipathic lipids function as a plasticizer for the sustained release coating materials, the plasticized sustained release coating materials can have a Tg of at least 25° C., 30° C., 35° C., 40° C., 45° C., 50° C., 55° C., 60° C., or 65° C. and/or not more than 150° C., 140° C., 130° C., 120° C., 110° C., 100° C., 90° C., 80° C., or 70° C. as measured using DSC. Thus, in one or more embodiments, the sustained release composition comprises at least one or more plasticized sustained release coating materials.

In certain embodiments, the tablets or multiparticulates do not contain an additional coating. In one or more embodiments, the tablets or multiparticulates do not contain a hydrophilic coating.

Exemplary Embodiments

Unless otherwise provided, the exemplary formulations described in this section may comprise any active ingredient, especially one or more of those specifically described above, any amphipathic lipid, any secondary sustained release agent, and any bulking or spheronizing agent. In addition, such exemplary formulations can be in tablet or multiparticulate forms and provide sustained release of the active ingredient.

In certain embodiments, the composition of the present disclosure in a tablet or multiparticulate form comprises, consists essentially of, or consists of: (a) from about 1% to about 70% by weight of an active ingredient; (b) from 1% to 30% by weight of one or more amphipathic lipids; (c) from about 10% to about 80% by weight of secondary sustained release agent, and (d) from about 5% to about 70% by weight of a bulking or spheronizing agent.

In certain embodiments, the composition of the present disclosure in a tablet or multiparticulate form comprises, consists essentially of, or consists of: (a) from about 0.5% to about 20% by weight of an active ingredient; (b) from about 0.5% to about 40% by weight of one or more amphipathic lipids; and (c) from about 10% to about 60% by weight of a one or more bulking or spheronizing agents.

In certain embodiments, the composition of the present disclosure in tablet or multiparticulate forms comprises, consists essentially of, or consists of: (a) from about 3% to about 25% by weight of an active ingredient; (b) from 1% to 15% by weight of one or more amphipathic lipids; (c) from about 5% to about 55% by weight of a secondary sustained release agent, and (d) from about 15% to about 45% by weight of a bulking or spheronizing agent.

In certain embodiments, the composition of the present disclosure in a tablet or multiparticulate form comprises, consists essentially of, or consists of: (a) from about 1% to about 80% by weight of an active ingredient; (b) from 1% to 30% by weight of phospholipids from an alcoholic dispersion; (c) from about 1% to about 70% by weight of hydrogenated vegetable oil, stearic acid, or vegetable wax, and (d) from about 5% to about 50% by weight of microcrystalline cellulose, pregelatinized starch, or a mixture thereof.

In certain embodiments, the composition of the present disclosure in a tablet or multiparticulate form comprises, consists essentially of, or consists of: (a) from about 3% to about 25% by weight of an active ingredient; (b) from 1% to 15% by weight of phospholipids from an alcoholic dispersion; (c) from about 1% to about 25% by weight of hydrogenated vegetable oil, stearic acid, or vegetable wax, and (d) from about 15% to about 45% by weight of microcrystalline cellulose, ethylcellulose, dicalcium phosphate or a mixture thereof.

In certain embodiments, the composition of the present disclosure in a tablet or multiparticulate form comprises, consists essentially of, or consists of: (a) from about 0.5% to about 20% by weight of phenylpropanolamine hydrochloride; (b) from 0.5% to 10% by weight of phospholipids from an alcoholic dispersion; (c) from about 10% to about 40% by weight of microcrystalline cellulose, and (d) from about 5% to about 25% by weight of dicalcium phosphate.

In certain embodiments, the composition of the present disclosure in a tablet or multiparticulate form comprises, consists essentially of, or consists of: (a) from about 1% to about 10% by weight of phenylpropanolamine hydrochloride; (b) from 5% to 25% by weight of phospholipids from an alcoholic dispersion; (c) from about 40% to about 65% by weight of hydrogenated vegetable oil or vegetable oil (e.g., hydrogenated cottonseed oil, stearic acid, and carnauba wax), (d) from about 15% to about 35% by weight of microcrystalline cellulose, and (e) from about 10% to about 20% by weight of dicalcium phosphate.

In certain embodiments, the composition of the present disclosure in a tablet or multiparticulate form comprises, consists essentially of, or consists of: (a) from about 1% to about 50% by weight of multi-vitamins and minerals, (b) from about 1% to about 25% by weight of phospholipids from an alcoholic dispersion, (c) from about 1% to about 20% by weight of hydrogenated vegetable oil or vegetable wax (e.g., hydrogenated cottonseed oil, stearic acid, or carnauba wax), and (d) from about 10% to about 50% by weight of microcrystalline cellulose.

In certain embodiments, the composition of the present disclosure in a tablet or multiparticulate form comprises, consists essentially of, or consists of: (a) from about 5% to about 30% by weight of a water-soluble drug or salt thereof, (b) from about 1% to about 25% by weight of phospholipids from an alcoholic dispersion, (c) from about 5% to about 50% by weight of hydrogenated vegetable oil or vegetable wax (e.g., hydrogenated cottonseed oil, stearic acid, or carnauba wax), and (d) from about 15% to about 60% by weight of microcrystalline cellulose.

In certain embodiments, the composition of the present disclosure in a tablet or multiparticulate form comprises, consists essentially of, or consists of: (a) about 8% or 9% by weight of phenylpropanolamine hydrochloride; (b) about 8.5% by weight of phospholipids from an alcoholic dispersion; (c) about 10% by weight of hydrogenated vegetable oil, stearic acid, or vegetable wax (e.g., hydrogenated cottonseed oil and carnauba wax), (d) about 24% by weight of microcrystalline cellulose, and (e) about 14% by weight of dicalcium phosphate.

In certain embodiments, the composition of the present disclosure in a tablet or multiparticulate form comprises, consists essentially of, or consists of: (a) about 8.25% by weight of phenylpropanolamine hydrochloride; (b) about 16.5% by weight of phospholipids from an alcoholic dispersion; (c) about 48% by weight of hydrogenated vegetable oil, stearic acid, or vegetable wax (e.g., hydrogenated cottonseed oil and carnauba wax), (d) about 24% by weight of microcrystalline cellulose, and (e) about 14% by weight of dicalcium phosphate.

In certain embodiments, the composition of the present disclosure in a tablet or multiparticulate form comprises, consists essentially of, or consists of: (a) about 10% by weight of phenylpropanolamine hydrochloride; (b) about 8.5% by weight of phospholipids from an alcoholic dispersion; (c) about 1 to about 10% by weight of hydrogenated vegetable oil, stearic acid, or vegetable wax (e.g., hydrogenated cottonseed oil and carnauba wax), (d) about 27% by weight of microcrystalline cellulose, and (e) about 24% by weight of dicalcium phosphate.

In certain embodiments, the composition of the present disclosure in a tablet or multiparticulate form comprises, consists essentially of, or consists of: (a) about 8.25% by weight of guaifenesin; (b) about 8.25% by weight of phospholipids from an alcoholic dispersion; (c) about 1% by weight of hydrogenated vegetable oil, stearic acid, or vegetable wax (e.g., hydrogenated cottonseed oil and carnauba wax), (d) about 25% by weight of microcrystalline cellulose, and (e) about 33% by weight of dicalcium phosphate.

In certain embodiments, the composition of the present disclosure in a tablet or multiparticulate form comprises, consists essentially of, or consists of: (a) about 0.9% by weight of dextromethorphan HBr; (b) about 8.25% by weight of phospholipids from an alcoholic dispersion; (c) about 1% by weight of hydrogenated vegetable oil, stearic acid, or vegetable wax (e.g., hydrogenated cottonseed oil and carnauba wax), (d) about 25% by weight of microcrystalline cellulose, and (e) about 40% by weight of dicalcium phosphate.

Dosage Forms

In another aspect, oral dosage forms that comprise the compositions disclosed herein are provided. The term "oral dosage form" refers to a device that collectively delivers, by oral ingestion, the desired amount of an active ingredient, to achieve a desired dose of the active ingredient. Typically, the oral dosage form is a powder for oral suspension, a unit dose packet or sachet, a tablet, or a capsule.

In certain embodiments, the pellets of the present disclosure may be mixed with a vehicle and packaged in a container such as a screw cap bottle. Prior to dosing, the mixture is added with water or another liquid and shaken to form an "oral suspension." In this oral suspension, the pellets containing the active ingredient may be (a) completely suspended in the vehicle, or (b) partially suspended in the vehicle and partially in solution with the vehicle.

In certain embodiments, the multiparticulate composition of the present disclosure may be mixed with or placed on feed to allow the animal patient to eat voluntarily.

The term "vehicle" refers to a mixture that facilitates the suspension of pellets and improves the taste of an oral suspension. A vehicle useful in this invention may contain suspending agents, anti-caking agents, fillers, sweeteners, flavorants, colorants, and/or lubricants.

Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and/or titanium dioxide.

Examples of anti-caking agents or fillers include colloidal silicon oxide and lactose.

In certain embodiments, the dosage form may be packaged in a bottle, packet, pouch, sachet, or capsule.

In certain embodiments, the dosage form comprises the active ingredient at a dose of at least about 10, 20, 50, 100, 200, 250, 300, 400, 500, 600, 700, 750, 800, or 900 mg, or about 1, 2, 3, 4, 5, 6, 7, 8, 9, or 10 gram per dose.

In certain embodiments, the dosage form is for single dose use. "Single dose," as used herein, refers to administering only one dose of an active ingredient in the full course of therapy.

In certain embodiments, the dosage form, upon oral administration to a patient in need thereof, provides a plasma concentration of the active agent in the patient at or above its minimum effective concentration for at least about 2, 4, 6, 8, 10, 12, 14, 16, 18, 20, 24, 36, 48, 72, 96, 120, 144, or 168 hours.

In certain embodiments, the dosage form, upon oral administration to a patient in need thereof, provides a plasma concentration of the active agent in the patient at or above its minimum effective concentration for a period of time that is at least about 2, 3, 4, or 5 times of that of an immediate release formulation administered at a standard dose.

Methods of Producing the Sustained Release Composition

In another aspect, the present disclosure provides a method for making the compositions and dosage forms described herein.

In certain embodiments, the present disclosure provides a method for making the sustained release composition that comprises: (a) combining one or more active ingredients, one or more amphipathic lipids, and any other optional ingredients discussed herein in a solvent to produce an active-containing solution or suspension; (b) mixing the active-containing solution or suspension with at least one spheronizing or bulking agent and any other optional ingredients discussed herein to produce a mixture; and (c) forming the mixture into tablets. In such an embodiment, steps (a)-(c) are performed at temperatures that do not exceed the melting point of the amphipathic lipids. The solvent can be selected from the group consisting of water, methanol, ethanol, n-propanol, isopropanol, t-butanol, ethyl acetate, acetone, and mixtures thereof.

In another embodiment, the method comprises: (a) combining one or more active ingredients, one or more amphipathic lipids, and any other optional ingredients discussed herein in a solvent to produce an active-containing solution or suspension; (b) mixing the active-containing solution or suspension with at least one spheronizing or bulking agent and any other optional ingredients discussed herein to produce a mixture; (c) granulating or extruding the mixture of step (b) to obtain wet granules or extrudates, (d) drying the granules or extrudates to produce a dry granule or extrudate, and (e) sizing the dry granules or fragmenting the dry extrudates to form pellets. In such an embodiment, steps (a)-(e) are performed at temperatures that do not exceed the melting point of the amphipathic lipids. In another embodiment, steps (a)-(e) are performed at temperatures that do not exceed 140° C., 130° C., 120° C., 110° C., 100° C., 90° C., 80° C., 70° C., 60° C., 50° C., 40° C., 35° C., or 30° C. In yet another embodiment, at least 75, 80, 85, 90, 95, 99, or 99.9 percent of the active ingredient added in step (a) remains present in the extrudates, granules, or pellets in steps (d) or (e).

In certain embodiments, the present disclosure provides a method for making the sustained release composition that comprises: (a) combining one or more active ingredients, one or more amphipathic lipids, one or more matrix-forming polymers, and any other optional ingredients discussed herein in a solvent to produce an active-containing solution or suspension; (b) mixing the active-containing solution or suspension with at least one spheronizing or bulking agent and any other optional ingredients discussed herein to produce a mixture; and (c) forming the mixture into tablets. In one embodiment, steps (a), (b), and/or (c) are performed at temperatures that do not exceed the melting point of the amphipathic lipids. In another embodiment, steps (a), (b), and/or (c) are performed at temperatures that exceed the glass transition temperature of the matrix-forming polymers. In such embodiments, steps (a), (b), and/or (c) can be performed at a temperature of at least about 30° C., 40° C., 50° C., 60° C., 65° C., or 70° C. In various embodiments, the matrix-forming polymers can comprise a spheronizing or bulking agent, a binder, a flavoring agent, a sustained coating material, or combinations thereof.

In another embodiment, the method comprises: (a) combining one or more active ingredients, one or more amphipathic lipids, one or more matrix-forming polymers, and any other optional ingredients discussed herein in a solvent to produce an active-containing solution or suspension; (b) mixing the active-containing solution or suspension with at least one spheronizing or bulking agent and any other optional ingredients discussed herein to produce a mixture; (c) granulating or extruding the mixture of step (b) to obtain wet granules or extrudates, (d) drying the granules or extrudates to produce a dry granule or extrudate, and (e) sizing the dry granules or fragmenting the dry extrudates to form pellets. In one embodiment, steps (a), (b), (c), (d), and/or (e) are performed at temperatures that do not exceed the melting point of the amphipathic lipids. In another embodiment, steps (a), (b), (c), (d), and/or (e) are performed at temperatures that do not exceed 140° C., 130° C., 120° C., 110° C., 100° C., 90° C., 80° C., 70° C., 60° C., 50° C., 40° C., 35° C., or 30° C. In yet another embodiment, steps (a), (b), (c), (d), and/or (e) are performed at temperatures that exceed the glass transition temperature of the matrix-forming polymers. In such embodiments, (a), (b), (c), (d), and/or (e) can be performed at a temperature of at least about 30° C., 40° C., 50° C., 60° C., 65° C., or 70° C. In various embodiments, the matrix-forming polymers can comprise a spheronizing or bulking agent, a binder, a flavoring agent, a sustained coating material, or combinations thereof.

In one embodiment, a binder is added in steps (a) and/or (b) during the method of making the compositions and dosage forms described herein. In another embodiment, a sustained coating material is added in steps (a) and/or (b) during the method of making the compositions and dosage forms described herein.

In certain embodiments, a plasticizer is added in steps (a) and/or (b) during the method of making the compositions and dosage forms described herein. Generally, in order to form a stable and functional barrier coat or matrix, the matrix which is formed during the process must be continuous and complete without any pores or cracks. In various embodiments, the matrix-forming polymers must be subjected to temperatures above the glass transition temperature of the matrix-forming polymer for continuous films to form. The glass transition temperature is a fundamental property of a polymeric system whereupon heating, the polymer changes from a brittle substance to a flexible rubber solid. Plasticizers are able to reduce the glass transition temperature of the matrix-forming polymers and enable the formation of a tough and flexible film without cracks. Thus, in embodiments where a plasticizer is introduced into the process and/or the amphipathic lipids function as a plasticizer, steps (a) and/or (b) can occur at a temperature that exceeds the glass transition temperature of the plasticized matrix-forming polymers. For example, in such embodiments, steps (a) and/or (b) can be performed at a temperature of at least about 30° C., 40° C., 50° C., 60° C., 65° C., or 70° C. Therefore, in various embodiments, the sustained release composition can comprise one or more plasticized matrix-forming polymers.

In one or more embodiments, the plasticizer comprises a solid state plasticizer. In various embodiments, the amphipathic lipids can function as the solid state plasticizer. In such embodiments, the amphipathic lipids can plasticize various components in the composition including, for example, matrix-forming polymers such as ethylcellulose. Ethylcellulose is a matrix-forming polymer that is used extensively in pharmaceutical systems. Generally, ethylcellulose is used to produce a barrier coat or matrix for controlling drug release. Unlike conventional liquid plasticizers, which have been shown to leach out of films, thereby causing stability issues over time, the amphipathic lipids can function as solid state plasticizers and mitigate such leaching.

As used herein, the term "granules" refers to small particles without approximately uniform shapes and sizes formed by the process in the present disclosure. Granules generally are less uniform in size or shape than pellets.

In certain embodiments, the dry granules or pellets are further filled into capsules.

In certain embodiments, the dry granules or pellets are further coated with a coating composition provided herein.

In certain embodiments, the dry granules or pellets are further mixed with other tableting ingredients and compressed into tablets. In other embodiments, the tablets are further coated with a coating composition provided herein.

The drying step is primarily used to remove water, hydroalcoholic, or organic solvent from the mixture and to cause the granules/extrudates/pellets to sufficiently harden. A lower temperature (e.g., no more than about 40° C., 35° C., or 30° C.) is usually sufficient for the drying purpose and is preferred for the stability of the active ingredient. In a preferred embodiment, the drying step does not occur at temperatures that exceed the melting points of the amphipathic lipids. For instance, the drying step does not exceed temperatures of 120° C., 110° C., 100° C., 80° C., 60° C., 50° C., 40° C., 35° C., or 30° C.

The drying time may vary from 10 minutes to several hours or longer depending upon the batch size, efficiency of the dryer used, and the drying temperature. The drying stage will continue until a substantial portion of the water, hydroalcoholic, or organic solvent has been removed from the granules or extrudates. As used herein, the term "dry," as used in conjunction with the granules, extrudates, and pellets, refers to granules, extrudates, or pellets having a residual solvent content of less than 10 weight percent. In other embodiments, the drying step can continue until the granules, extrudates, or pellets contain a residual solvent content of no more than 7, 5, or 3 weight percent.

In certain embodiments, the drying step may be performed in a lyophilizer, fluid bed process, convection oven, or microwave oven.

In certain embodiments, the method of the present disclosure does not utilize a heating step that uses temperatures exceeding the melting points of the amphipathic lipids. In such an embodiment, the active ingredients exhibit little or no degradation during the production method provided herein.

In certain embodiments, the dry granules, pellets, extrudates, or tablets produced via the above extrusion process are further coated with a coating composition. Such a coating composition may comprise amphipathic lipids, a secondary sustained release agent, a flavorant, a colorant, or a combination thereof.

Methods of Using Compositions

In one aspect, the present disclosure provides methods for using the sustained release compositions and dosage forms described herein for treating or preventing diseases or disorders. The diseases or disorders include, for example, incontinence, congestion, hypothyroidism, hyperthyroidism, anxiety, depression and other behavioral disorders, pain, inflammation, infection, diabetes, hyperphosphataemia, chronic diseases, and dietary deficiencies. As previously mentioned, the sustained release composition described herein can be used to treat diseases or disorders in human or non-human patients.

This invention can be further illustrated by the following examples of embodiments thereof, although it will be understood that these examples are included merely for the purposes of illustration and are not intended to limit the scope of the invention unless otherwise specifically indicated.

ENABLING EXAMPLES

The following examples are provided by way of illustration, and not by way of limitation.

Example 1

Chewable sustained release tablets containing PPA were prepared by first mixing phospholipids (PHOSPHOLIPON 90, "PL90H") with a PPA dissolved in ethanol at about 30° C. to about 40° C. to produce a dispersion. Using a low-shear mixer, microcrystalline cellulose, liver blend, and dicalcium phosphate were mixed with the dispersion to produce a wet-mass material. Extrudates (i.e., wet granules) were produced by passing the wet-mass material through a 16-mesh screen. The granules were dried at ambient temperature over night until the moisture level was not more than 7% by weight. The dried granules were then further fragmented by forcing them through a 10-mesh screen sieve. The sized granules were then mixed with a lubricating stearic acid. Finally, the granules were compressed into tablets having the target weight and exhibiting a hardness of less than 20 kP. The sustained release tablets contained PPA and varying amounts of phospholipids as shown in TABLE 1. The PPA potency in each of the tablet samples was calculated using a RP-HPLC method.

TABLE 1

| Component | 1:2 PPA:PL90H | 1:1 PPA:PL90H | HPMC |
|---|---|---|---|
| PPA | 8.25% | 8.25% | 8.25% |
| PHOSPHOLIPON 90H | 16.5% | 8.25% | — |
| HPMC | — | — | 40% |
| Dicalcium Phosphate | 33% | 33% | 44.75% |
| Microcrystalline Cellulose | 24.75% | 24.75% | 6% |
| Liver Blend | 16.5% | 24.75% | — |
| Stearic Acid | 1% | 1% | 1% |
| Total Tablet Weight % | 100% | 100% | 100% |

The in vitro dissolution profiles of the sustained release tablets were tested by using a USP Dissolution Apparatus II. Each tested sample was filtered through a 10 micron filter prior to testing. The in vitro dissolution profiles of the sustained release tablets were compared to PPA extended release tablets comprising hypromellose ("HPMC"), 100 mg PPA, and no phospholipids. The formulation of this tablet is shown in TABLE 1. The in vitro dissolution profiles of the sustained release tablets of TABLE 1 are presented in FIG. 1. The tablets containing 16.5% and 8.25% of phospholipids demonstrated similar dissolution rates to the HPMC tablet. Both of these formulations continuously released PPA over a period of 16 hours, thus meeting USP criteria for PPA extended release tablets.

Example 2

This example focused on the effects that PHOSPHOLIPON 20 had on the in vitro dissolution of the chewable sustained release tablets. Sustained release tablets were prepared using the method outlined in Example 1. The sustained release tablets contained 100 mg of PPA and varying amounts of phospholipids (PHOSPHOLIPON 20, "PL20") as shown in TABLE 2. The PPA potency of the tablets was confirmed using the method outlined in Example 1.

TABLE 2

| Component | 1:1 PPA:Phospholipon 20 | 1:2 PPA:Phospholipon 20 | 1:3 PPA:Phospholipon 20 |
|---|---|---|---|
| PPA | 8.25% | 8.25% | 8.25% |
| PHOSPHOLIPON 20 | 8.25% | 16.5% | 24.75% |
| Dicalcium Phosphate | 33% | 30% | 30% |
| Microcrystalline Cellulose | 24.75% | 21.75% | 13.75% |
| Liver Blend | 24.75% | 22% | 22% |
| Stearic Acid | 1% | 1% | 1% |
| Total Tablet Weight % | 100% | 100% | 100% |

Figure 2:
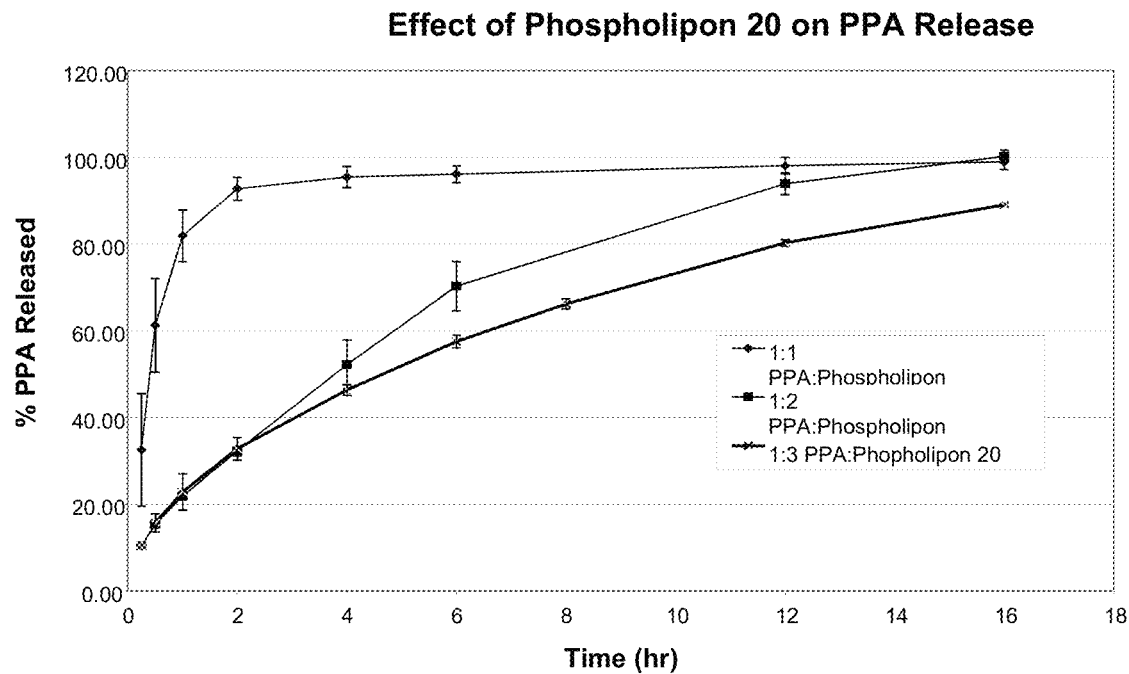
FIG. 2. depicts in vitro dissolution profiles of PPA sustained release tablets at two different phospholipid concentrations.

The in vitro dissolution profiles of the sustained release tablets were tested as outlined in Example 1. The in vitro dissolution profiles of the sustained release tablets in TABLE 2 are presented in FIG. 2. The tablets containing 24.75% and 16.5% of PHOSPHOLIPON 20 demonstrated similar dissolution rates to the HPMC PPA tablet of Example 1. Both of these formulations consistently released PPA over a period of 16 hours, thus meeting USP criteria for PPA extended release tablets.

Example 3

This example focused on the effects that different types of lecithin have on the in vitro dissolution of the chewable sustained release tablets. Sustained release tablets were prepared using the method outlined in Example 1. The sustained release tablets contained 100 mg of PPA and lecithin from either BULKFOODS.COM or ULTRALEC as shown in TABLE 3. The PPA potency of the tablets was confirmed using the method outlined in Example 1.

TABLE 3

| Component | 1:2 PPA:LEC | 1:2 PPA:ULTRALEC |
|---|---|---|
| PPA | 8.25% | 8.25% |
| BULKFOODS.COM lecithin | 16.5% | — |
| ULTRATEC lecithin | — | 16.5% |
| Dicalcium Phosphate | 33% | 33% |
| Microcrystalline Cellulose | 16.5% | 16.5% |
| Liver Blend | 24.75% | 24.75% |
| Stearic Acid | 1% | 1% |
| Total Tablet Weight % | 100% | 100% |

Figure 3:
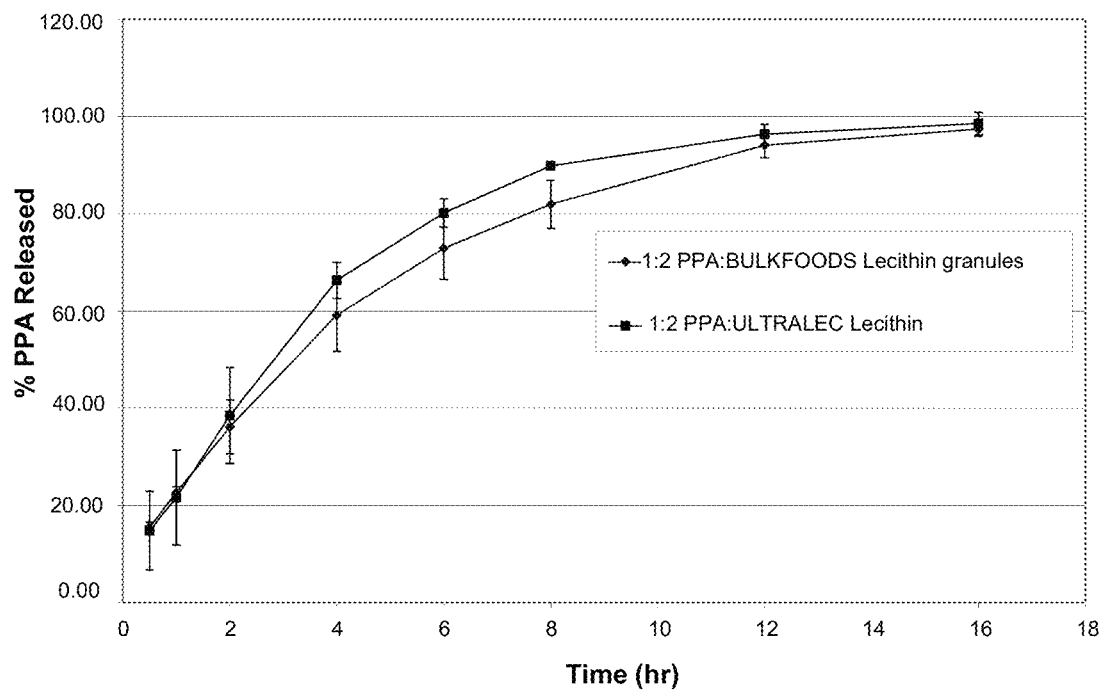
FIG. 3. depicts in vitro dissolution profiles of PPA sustained release tablets formulated with two different types of lecithin.

The in vitro dissolution profiles of the sustained release tablets were tested as outlined in Example 1. The in vitro dissolution profiles of the sustained release tablets in TABLE 3 are presented in FIG. 3. Both sustained release tablets containing lecithin consistently released PPA over a period of 16 hours, thus meeting USP criteria for PPA extended release tablets.

Example 4

This example focused on the production of chewable sustained release tablets containing PPA with taste-masking properties. The sustained release tablets were produced by adding and dissolving PPA in isopropanol at about 30° C. Cholesterol was then added and dissolved in the mixture. Subsequent to dissolving the cholesterol, phospholipids (PHOSPHOLIPON 20) were added to the mixture to thereby produce a homogeneous dispersion. Separately, the dry ingredients (i.e., dicalcium phosphate, microcrystalline cellulose, and liver blend) were added to a low shear mixer and mixed together. The isopropanol mixture was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets having the target weight of 1,200 mg and exhibiting a hardness of less than 20 kP. The produced tablets were 1.2 g in weight and round in shape and were suitable for administration to animals for the condition of incontinence. As shown in TABLE 4, the produced tablets contained cholesterol and, in some cases, a mixture of phospholipids. The PPA potency of the tablets was confirmed using the method outlined in Example 1.

TABLE 4

| Component | 1:1 PPA:Cholesterol | 1:1/2:1/2 PPA:Cholesterol/PL 20 | 1:3/2:3/2 PPA:Cholesterol/PL 20 |
|---|---|---|---|
| PPA | 8.25% | 8.25% | 8.25% |
| Cholesterol | 8.25% | 4.13% | 5.5% |
| Phospholipon 20 | 0% | 4.13% | 5.5% |
| Dicalcium Phosphate | 33% | 33% | 33% |
| Microcrystalline Cellulose | 24.75% | 24.75% | 23.4% |
| Liver Blend | 25.75% | 25.75% | 24.75% |
| Total Tablet Weight % | 100% | 100% | 100% |

Figure 4:
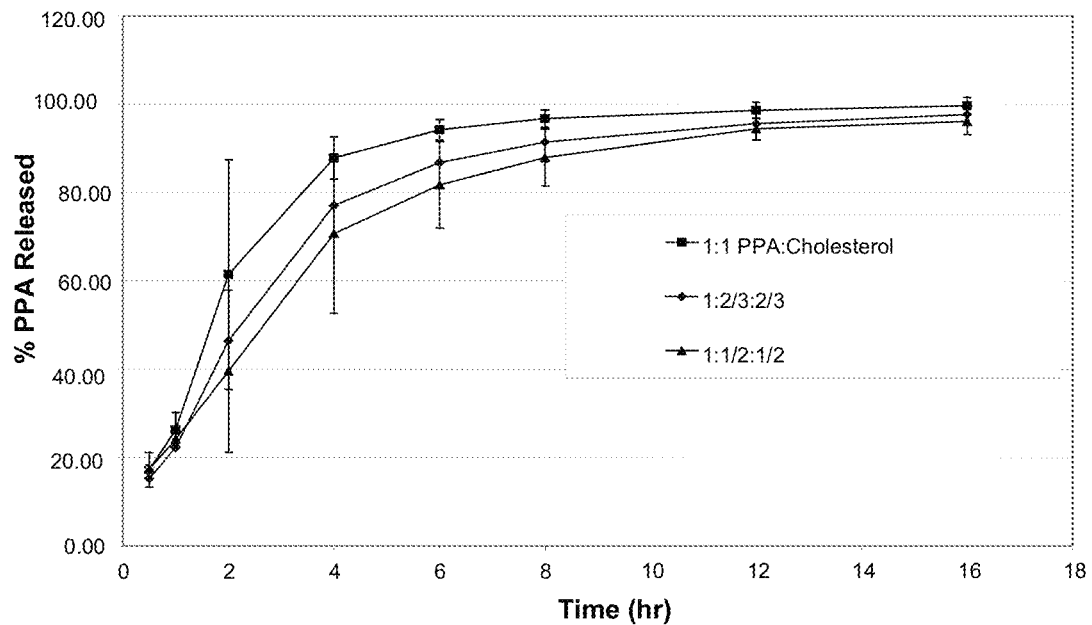
FIG. 4. depicts in vitro dissolution profiles of PPA sustained release tablets formulated with cholesterol and phospholipids.

The in vitro dissolution profiles of the sustained release tablets were tested as outlined in Example 1. As shown in FIG. 4, the combination of cholesterol and phospholipids provided a sustained release of PPA over the course of about 16 hours. In addition, the mixture of cholesterol and phospholipids in the tablets provided an effective taste-masking barrier to the bitter tasting PPA.

Example 5

This example focused on the production of chewable PPA sustained release tablets containing phospholipids and ethylcellulose. The sustained release tablets were produced by adding and dissolving PPA in ethanol at 40° C. Ethylcellulose and phospholipids (PHOSPHOLIPON 90H) were then added to the PPA/ethanol solution and mixed in until a homogenous liquid was obtained without any visible solid particles. Separately, the dry ingredients (i.e., dicalcium phosphate, microcrystalline cellulose, and roast beef flavor) were added to a low shear mixer and mixed together. The ethanol-based homogenous liquid was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets with a 1.6 cm circular biconvex punch/die. As shown in TABLE 5, the produced tablets contained ethylcellulose and phospholipids as the sustained release agents. The PPA potency of the tablets was confirmed using the method outlined in Example 1.

TABLE 5

| Component | 1% Ethylcellulose | 3% Ethylcellulose |
|---|---|---|
| PPA | 8.25% | 8.25% |
| PHOSPHOLIPON 90H | 5.5% | 5.5% |
| Ethylcellulose | 1% | 3% |
| Dicalcium Phosphate | 50% | 50% |
| Microcrystalline Cellulose | 30.2% | 28.2% |
| Roast Beef Flavor | 5% | 5% |
| Total Tablet Weight % | 100% | 100% |

Figure 5:
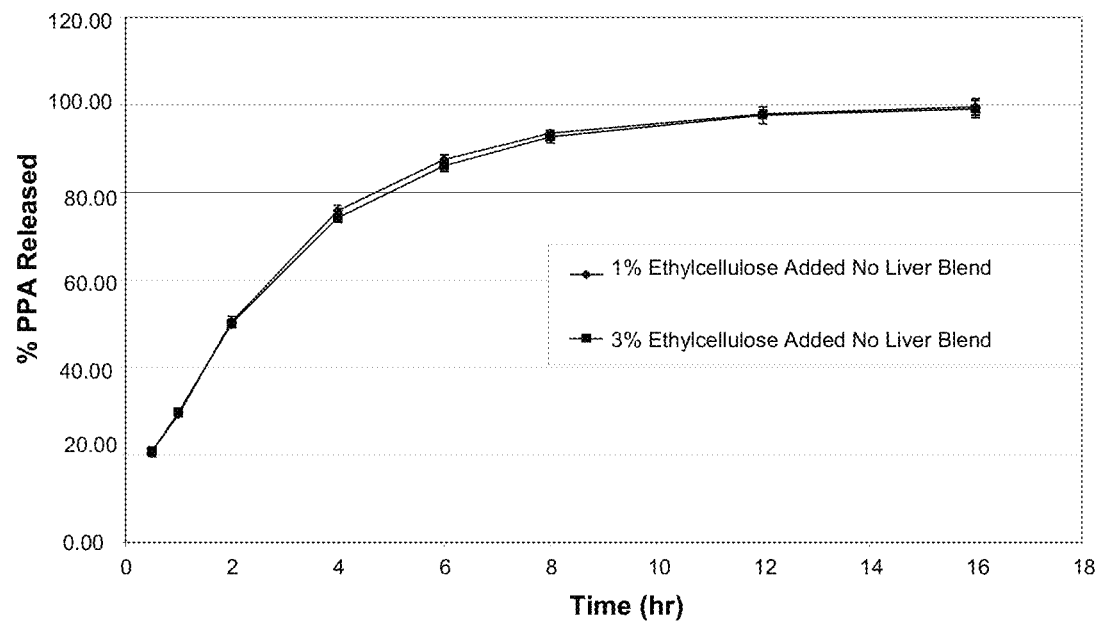
FIG. 5. depicts in vitro dissolution profiles of PPA sustained release tablets formulated with about 1% and 3% ethylcellulose plasticized with phospholipids.

The in vitro dissolution profiles of the sustained release tablets were tested as outlined in Example 1. As depicted in FIG. 5, the combination of ethylcellulose and phospholipids provide a sustained release of PPA over the course of about 16 hours. Furthermore, these results indicate that phospholipids are a good plasticizer for ethylcellulose films, which are used to encapsulate the PPA. Consequently, the ethylcellulose is able to form a continuous and flexible controlled release barrier for the PPA during dissolution. Additionally, the ethylcellulose plasticized with phospholipids showed flexibility that is equivalent to ethylcellulose films cast with traditional plasticizers such as triethyl citrate and dibutyl phthalate.

Example 6

This example focused on the production of chewable PPA sustained release tablets containing glyceryl behenate. The sustained release tablets were produced by adding and dissolving PPA in ethanol at 40° C. Glyceryl behenate (COMPRITOL 888 ATO) was added and mixed into the PPA/ethanol solution. After mixing in the glyceryl behenate, phospholipids (PHOSPHOLIPON 90) were then added and mixed in until a crude emulsion was obtained. Separately, the dry ingredients (i.e., dicalcium phosphate, microcrystalline cellulose, and roast beef flavor) were added to a low shear mixer and mixed together. The crude emulsion was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets having the target weight of 1.2 g and exhibiting a hardness of less than 20 kP. As shown in TABLE 6, the produced tablets contained varying amounts of glyceryl behenate. The PPA potency of the tablets was confirmed using the method outlined in Example 1.

TABLE 6

| Component | 5% Glyceryl Behenate | 10% Glyceryl Behenate |
|---|---|---|
| PPA | 8.25% | 8.25% |
| PHOSPHOLIPON 90H | 5.5% | 5.5% |
| Dicalcium Phosphate | 50% | 50% |
| Microcrystalline Cellulose | 25.2% | 20.2% |
| Roast Beef Type Flavor | 5% | 5% |
| Stearic Acid | 1% | 1% |
| Compritol 888 ATO | 5% | 10% |
| Total Tablet Weight % | 100% | 100% |

Figure 6:
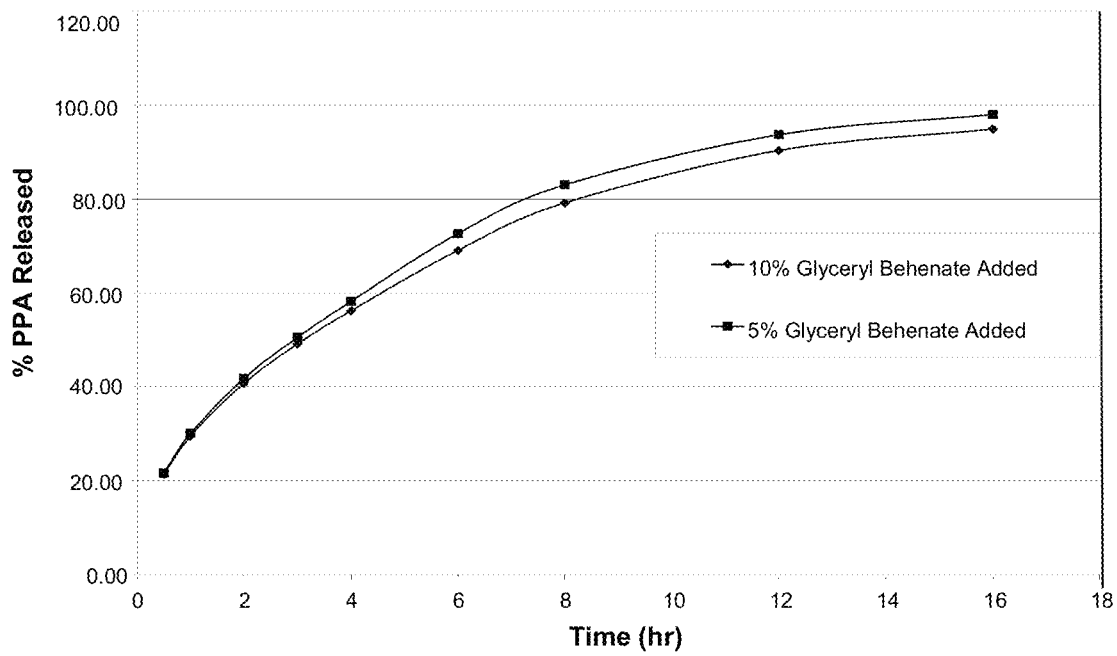
FIG. 6. depicts in vitro dissolution profiles of PPA sustained release tablets formulated with phospholipids and 5% and 10% glyceryl behenate.

The produced tablets were broken into four parts and then subjected to in vitro dissolution analysis as outlined in Example 1. As depicted in FIG. 6, the tablets containing glyceryl behenate consistently released PPA over a period of 16 hours, thus meeting USP criteria for PPA extended release tablets.

Example 7

This example focused on the production of chewable PPA sustained release tablets containing hydrogenated cottonseed oil. The sustained release tablets were produced by adding and dissolving PPA in ethanol at 30° C. Hydrogenated cottonseed oil (STEROTEX NF) was added and mixed into the PPA/ethanol solution. After mixing in the hydrogenated cottonseed oil, phospholipids (PHOSPHOLIPON 90) were then added and mixed in until a crude emulsion was obtained. Separately, the dry ingredients (i.e., dicalcium phosphate, microcrystalline cellulose, and roast beef flavor) were added to a low shear mixer and mixed together. The crude emulsion was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets having the target weight of 1.2 g and exhibiting a hardness of less than 20 kP. As shown in TABLE 7, the produced tablets contained varying amounts of hydrogenated cottonseed oil. The PPA potency of the tablets was confirmed using the method outlined in Example 1.

TABLE 7

| Component | 10% Sterotex Granulation | 20% Sterotex Granulation |
|---|---|---|
| PPA | 8.25% | 8.25% |
| Phospholipon 20 | 16.5% | 16.5% |
| Dicalcium Phosphate | 40% | 35% |
| Microcrystalline Cellulose | 19.2% | 14.2% |
| Roast Beef Type Flavor | 5% | 5% |
| STEROTEX NF | 10% | 20% |
| Stearic Acid | 1% | 1% |
| Total Tablet Weight % | 100% | 100% |

Figure 7:
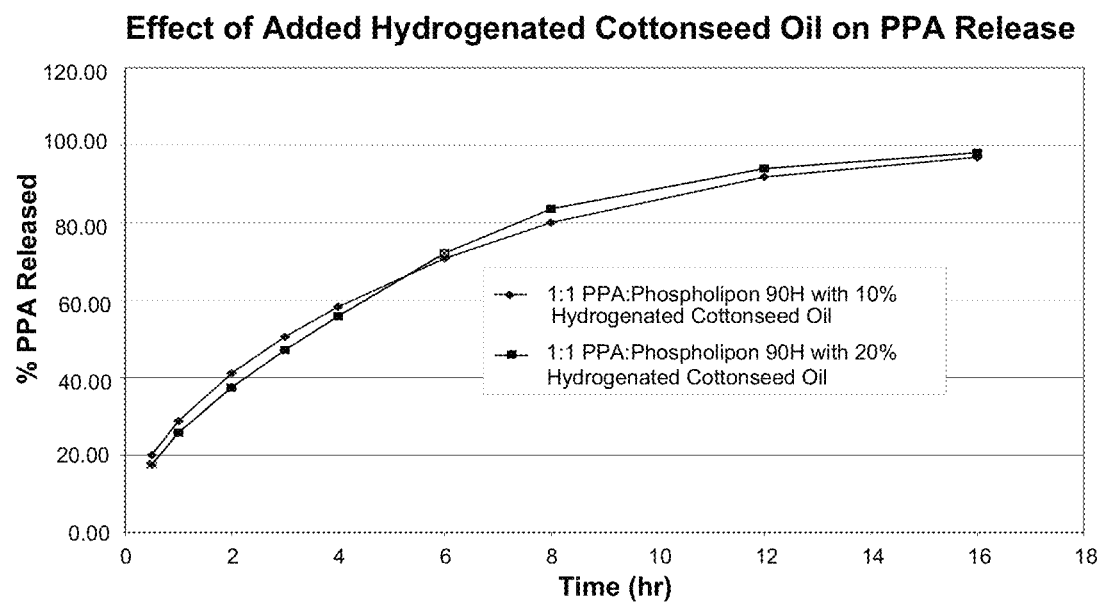
FIG. 7. depicts in vitro dissolution profiles of PPA sustained release tablets formulated with phospholipids and 10% and 20% hydrogenated cottonseed oil.

The produced tablets were broken into four parts and then subjected to in vitro dissolution analysis as outlined in Example 1. As depicted in FIG. 7, the tablets containing hydrogenated cottonseed oil consistently released PPA over a period of 16 hours, thus meeting USP criteria for PPA extended release tablets.

Example 8

This example focused on the production of chewable sustained release tablets containing guaifenesin. The sustained release tablets were produced by adding and dissolving guaifenesin in ethanol at 30° C. Phospholipids (PHOSPHOLIPON 90) were added and mixed in until a crude emulsion was obtained. Separately, the dry ingredients (i.e., dicalcium phosphate, microcrystalline cellulose, and liver blend) were added to a low shear mixer and mixed together. The crude emulsion was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets having the target weight of 1.2 g and exhibiting a hardness of less than 20 kP.

TABLE 8

| Component | Guaifenesin Tablet |
| --- | --- |
| Guaifenesin | 8.25% |
| PHOSPHOLIPON 90H | 8.25% |
| Dicalcium Phosphate | 33% |
| Microcrystalline Cellulose | 24.75% |
| Liver Blend | 24.75% |
| Stearic Acid | 1% |
| Total Tablet Weight % | 100% |

Figure 8:
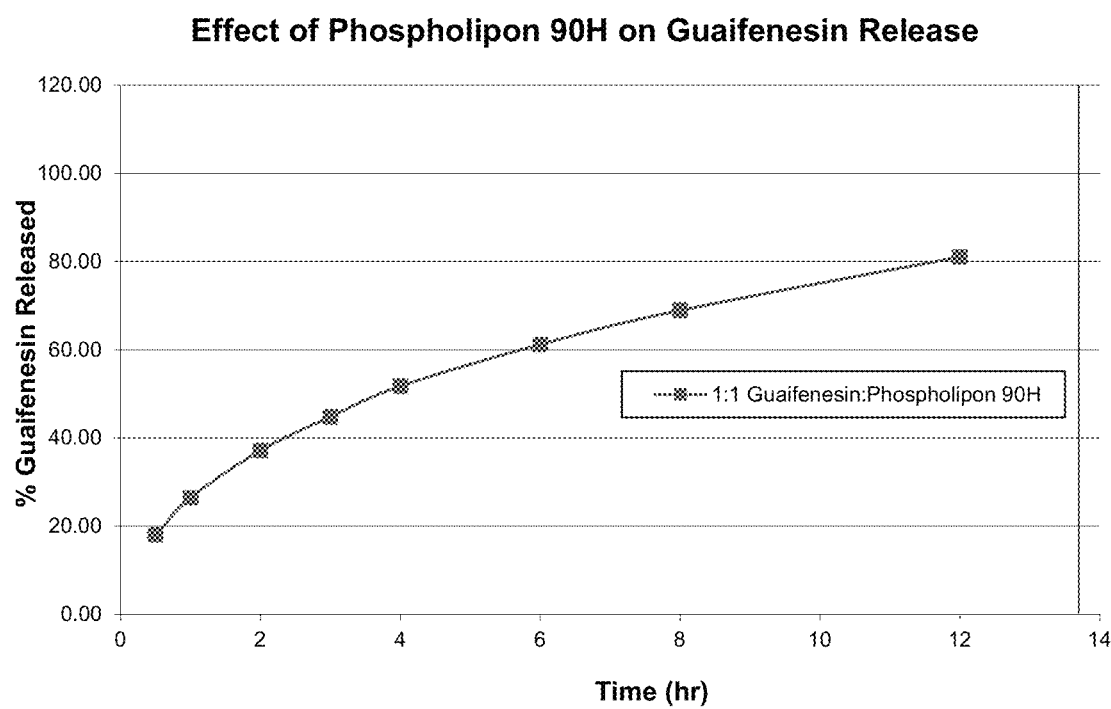
FIG. 8. depicts in vitro dissolution profiles of guaifenesin sustained release tablets formulated with phospholipids.

The produced tablets formed with guaifenesin contained the formulation as depicted in TABLE 8. The guaifenesin potency of the tablets was confirmed using the method outlined in Example 1. The produced tablets were broken into four parts and then subjected to in vitro dissolution analysis as outlined in Example 1. As shown in FIG. 8, the tablets consistently released guaifenesin over a period of 12 hours, thus meeting USP criteria for guaifenesin extended release tablets.

Example 9

This example focused on the production of sustained release tablets containing dextromethorphan. The sustained release tablets were produced by adding and dissolving dextromethorphan in ethanol at 30° C. Phospholipids (PHOSPHOLIPON 90) were added and mixed in until a crude emulsion was obtained. Separately, the dry ingredients (i.e., dicalcium phosphate, microcrystalline cellulose, and liver blend) were added to a low shear mixer and mixed together. The crude emulsion was then added to the dry ingredients and mixed until a homogeneous mixture was produced. The homogenous mixture was passed through a 16-mesh screen and the produced granules were dried at ambient temperature overnight. The dried granules were further fragmented by forcing them through a 10-mesh screen sieve. The sized granules were then mixed with a lubricating stearic acid. Finally, the granules were compressed into tablets having the target weight of 1.2 g and exhibiting a hardness of less than 20 kP.

TABLE 9

| Component | Dextromethorphan Tablet |
| --- | --- |
| Dextromethorphan HBr | 0.83% |
| PHOSPHOLIPON 90H | 8.25% |
| Dicalcium Phosphate | 40% |
| Microcrystalline Cellulose | 24.75% |
| Liver Blend | 24.75% |
| Stearic Acid | 1% |
| Total Tablet Weight % | 100% |

Figure 9:
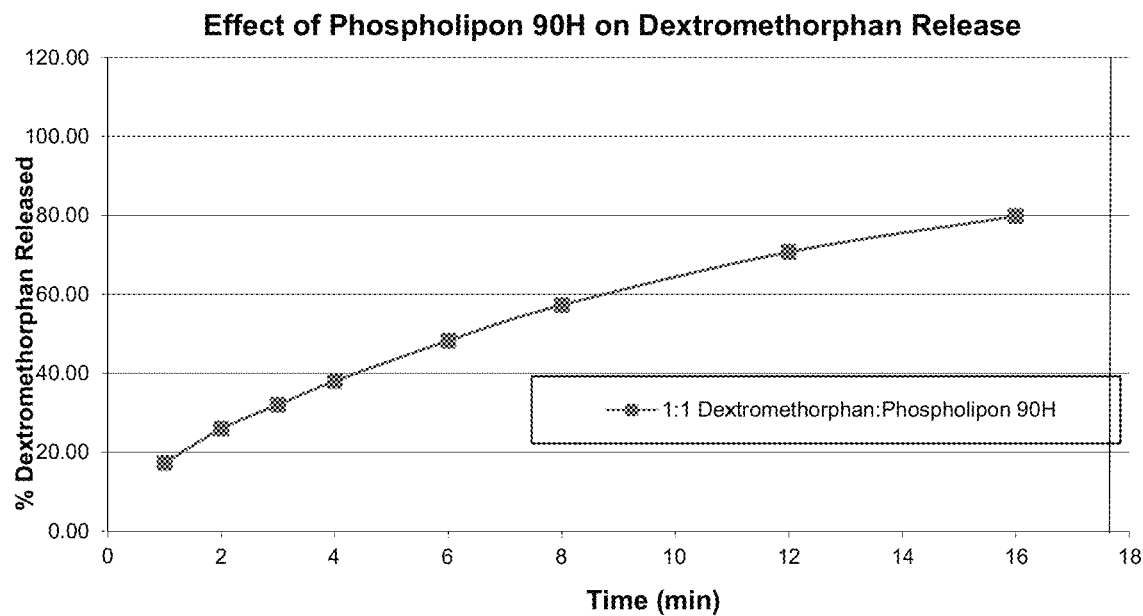
FIG. 9. depicts in vitro dissolution profiles of dextromethorphan HBr sustained release tablets formulated with phospholipids.

The produced tablets formed with dextromethorphan contained the formulation as depicted in TABLE 9. The produced tablets were broken into four parts and then subjected to in vitro dissolution analysis as outlined in Example 1. As shown in FIG. 9, the tablets consistently released dextromethorphan over a period of 12 hours, thus meeting USP criteria for dextromethorphan extended release tablets.

Example 10

This example focused on the production of sustained release tablets containing PPA as shown in Table 10. The sustained release tablets were produced by adding and dissolving ethylcellulose, phospholipids (PHOSPHOLIPON 90H and PHOSPHOLIPON 20), and PPA in ethanol at 70° C. to form a dispersion. Separately, the dry ingredients (i.e., dicalcium phosphate, microcrystalline cellulose, dried chicken liver powder, dry garlic flavor, and dark brown lake blend) were added to a low shear mixer and mixed together. The liquid dispersion was then added to the dry ingredients and mixed until a homogeneous mixture was produced. The homogenous mixture was passed through a 16-mesh screen and the produced granules were dried at ambient temperature overnight. The sized granules were then mixed with a lubricating magnesium stearate. Finally, the granules were compressed into tablets having the target weight of 500 mg and exhibiting a hardness of less than 20 kP.

TABLE 10

| Component | PPA Tablet Composition |
| --- | --- |
| Phenylpropanolamine HCl | 10% |
| PHOSPHOLIPON 90H | 3% |
| PHOSPHOLIPON 20 | 3.5% |
| Ethylcellulose | 2% |
| Dicalcium Phosphate | 39.8% |
| Microcrystalline Cellulose | 27.2% |
| Dried Powdered Chicken Liver | 11% |
| Dry Garlic Flavor | 2% |
| Dark Brown Lake Blend | 0.5% |
| Magnesium Stearate | 1% |
| Total Tablet Weight % | 100% |

Figure 10:
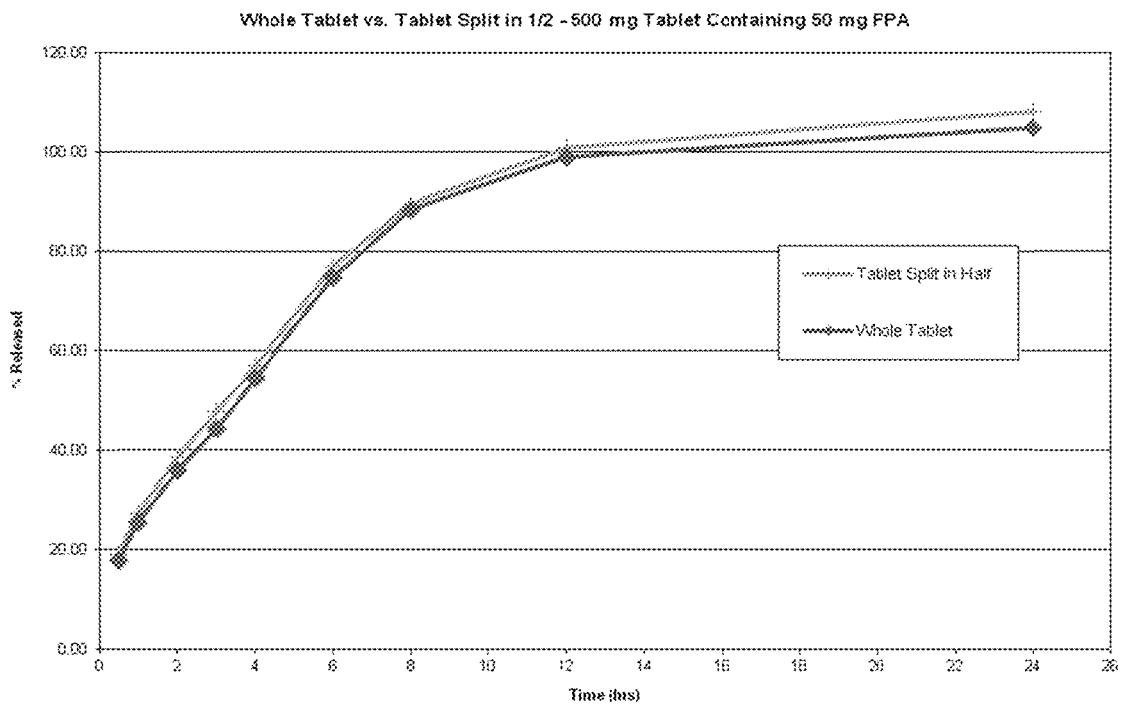
FIG. 10. depicts in vitro dissolution profiles of whole PPA sustained release tablets versus tablets when broken in half.

The produced tablets formed with PPA contained the formulation as depicted in TABLE 10. The produced tablets were broken into two parts and then subjected to in vitro dissolution analysis as outlined in Example 1. As shown in FIG. 10, the tablets consistently released PPA over a period of 24 hours, thus meeting USP criteria for PPA extended release tablets.

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

We claim:
1. A composition comprising:
(a) one or more active ingredients;
(b) 3 to 50 weight percent of one or more amphipathic lipids;
(c) 30 to 90 weight percent of at least one bulking or spheronizing agent selected from the group consisting of microcrystalline cellulose, starch, sodium carboxymethylcellulose, pregelatinized starch, dicalcium phosphate, powdered sugar, calcium phosphate, cal- cium sulfate, lactose, mannitol, kaolin, sodium chloride, sorbitol, and combinations thereof;
(d) 0.1 to 25 weight percent of at least one matrix-forming binder comprising a glass transition temperature of 130 to 250° C.; and
(e) 3 to 40 weight percent of a plasticized flavoring agent comprising a matrix-forming polymer,
wherein said active ingredients being encapsulated within a continuous matrix comprising said amphipathic lipids, said bulking or spheronizing agent, and said plasticized matrix-forming binder,
wherein said composition exhibits an in vitro dissolution rate of said active ingredients as measured by a USP Dissolution Apparatus II of about 10% to 50% after about 2 hours, about 25% to 90% after about 4 hours, more than about 60% after about 12 hours, and more than about 75% after about 16 hours,
wherein the average in vitro dissolution rate of said composition as measured by a USP Dissolution Apparatus II does not increase by more than 100% during the first 2 hours after said composition has been fragmented into two or more pieces, and
wherein said amphipathic lipids plasticize said matrix-forming binder to thereby form a plasticized matrix-forming binder comprising a plasticized glass transition temperature that is at least 25 percent lower than said glass transition temperature of said matrix-forming binder.

2. A composition comprising:
(a) one or more active ingredients;
(b) 3 to 50 weight percent of one or more amphipathic lipids;
(c) 30 to 90 weight percent of at least one bulking or spheronizing agent selected from the group consisting of microcrystalline cellulose, starch, sodium carboxymethylcellulose, pregelatinized starch, dicalcium phosphate, powdered sugar, calcium phosphate, calcium sulfate, lactose, mannitol, kaolin, sodium chloride, sorbitol, and combinations thereof;
(d) 0.1 to 25 weight percent of at least one matrix-forming binder comprising a glass transition temperature of 130 to 250° C.; and
(e) 3 to 40 weight percent of a plasticized flavoring agent comprising a matrix-forming polymer,
wherein said at least one active ingredient being encapsulated within a single continuous matrix comprising a mixture of said amphipathic lipids, said matrix-forming binder, and said bulking or spheronizing agent,
wherein said composition exhibits an in vitro dissolution rate of said active ingredients as measured by a USP Dissolution Apparatus II of about 10% to 50% after about 2 hours, about 25% to 90% after about 4 hours, more than about 60% after about 12 hours, and more than about 75% after about 16 hours,
wherein the average in vitro dissolution rate of said composition as measured by a USP Dissolution Apparatus II does not increase by more than 100% during the first 2 hours after said composition has been fragmented into two or more pieces, and
wherein said amphipathic lipids plasticize said matrix-forming binder to thereby form a plasticized matrix-forming binder comprising a plasticized glass transition temperature of 50 to 150° C.

3. A method for preparing tablets of a sustained release composition comprising:
(a) dissolving one or more active ingredients, one or more amphipathic lipids, and at least one matrix-forming binder in a solvent to produce an active-containing solution or suspension;
(b) mixing said active-containing solution or suspension with at least one spheronizing or bulking agent and a flavoring agent comprising a matrix-forming polymer to produce a homogenous mixture,
wherein said spheronizing or bulking agent is selected from the group consisting of microcrystalline cellulose, starch, sodium carboxymethylcellulose, pregelatinized starch, dicalcium phosphate, powdered sugar, calcium phosphate, calcium sulfate, lactose, mannitol, kaolin, sodium chloride, sorbitol, and combinations thereof,
wherein said amphipathic lipids plasticize said matrix-forming polymer during said mixing to thereby form a plasticized matrix-forming polymer; and
(c) forming said homogenous mixture into tablets,
wherein said composition exhibits an in vitro dissolution rate of said active ingredients as measured by a USP Dissolution Apparatus II about 10% to 50% after about 2 hours, about 25% to 90% after about 4 hours, more than about 60% after about 12 hours, and more than about 75% after about 16 hours,
wherein the average in vitro dissolution rate of said composition as measured by a USP Dissolution Apparatus II does not increase by more than 100% during the first 2 hours after said composition has been fragmented into two or more pieces,
wherein said steps (a)-(c) are performed at temperatures not exceeding the melting point of said amphipathic lipids,
wherein said composition comprises (i) 3 to 50 weight percent of said amphipathic lipids, (ii) 30 to 90 weight percent of said spheronizing or bulking agent, (iii) 0.1 to 25 weight percent of said plasticized matrix-forming binder, and (iv) 3 to 40 weight percent of said flavoring agent,
wherein said matrix-forming binder comprises a pre-plasticized glass transition temperature of 130 to 250° C., and
wherein said plasticized matrix-forming binder comprises a plasticized glass transition temperature that is at least 25 percent lower than said pre-plasticized glass transition temperature.

4. The composition according to claim 1 wherein the average in vitro dissolution rate of said composition as measured by a USP Dissolution Apparatus II does not increase by more than 50% during the first 2 hours after said composition has been fragmented into two or more pieces.

5. The composition according to claim 1 wherein said plasticized matrix-forming binder has a glass transition temperature is in the range of 50 to 150° C.

6. The composition according to claim 1 wherein said one or more amphipathic lipids are selected from the group consisting of phospholipids, lecithins, ceramides, sphingolipids, steroids, and glycolipids.

7. The composition according to claim 1 wherein said plasticized matrix-forming binder comprises ethylcellulose.

8. The composition according to claim 1 wherein said composition does not exhibit a delayed dissolution profile in environments having a pH of less than about 7.

9. A tablet comprising the composition according to claim 1 wherein said tablet is not coated with a hydrophilic coating.

10. The composition according to claim 2 wherein said plasticized matrix-forming binder has a plasticized glass transition temperature of not more than about 100° C.

11. The composition according to claim 2 wherein said one or more amphipathic lipids are selected from the group consisting of phospholipids, lecithins, ceramides, sphingolipids, steroids, and glycolipids.

12. The composition according to claim 2 wherein said composition does not exhibit a delayed dissolution profile in environments having a pH of less than about 7.

13. The method according to claim 3 wherein said plasticized glass transition temperature is in the range of 50 to 150° C.

14. The method according to claim 3 wherein said matrix-forming binder comprises ethylcellulose.

15. The method according to claim 3 wherein said tablets comprise a continuous matrix that contains said amphipathic lipids, said bulking or spheronizing agent, and said plasticized matrix-forming binder, wherein said active ingredients are encapsulated within said matrix.

16. The method according to claim 3 wherein said step (a) is performed at a temperature of at least 40° C.

17. The composition according to claim 1 wherein said matrix-forming polymer comprises collagen.

18. The composition according to claim 2 wherein said matrix-forming polymer comprises collagen.

19. The method according to claim 3 wherein said matrix-forming polymer comprises collagen.

* * * * *